(12) United States Patent
Breivik et al.

(10) Patent No.: US 9,145,533 B2
(45) Date of Patent: Sep. 29, 2015

(54) PROCESS FOR CONCENTRATING OMEGA-3 FATTY ACIDS

(75) Inventors: Harald Breivik, Inndyr (NO); Olav Thorstad, Porsgrunn (NO); Fred Olav Libnau, Bergen (NO)

(73) Assignee: Pronova Blopharm Norge AS, Lysaker (NO)

( * ) Notice: Subject to any disclaimer, the term of this patent is extended or adjusted under 35 U.S.C. 154(b) by 148 days.

(21) Appl. No.: 13/825,739

(22) PCT Filed: Sep. 23, 2011

(86) PCT No.: PCT/IB2011/002593
§ 371 (c)(1),
(2), (4) Date: Aug. 12, 2013

(87) PCT Pub. No.: WO2012/038833
PCT Pub. Date: Mar. 29, 2012

(65) Prior Publication Data
US 2013/0317241 A1 Nov. 28, 2013

Related U.S. Application Data

(60) Provisional application No. 61/386,096, filed on Sep. 24, 2010.

(51) Int. Cl.
*C07C 51/43* (2006.01)
*C11B 3/00* (2006.01)
*C07C 51/48* (2006.01)
*C07C 51/50* (2006.01)

(52) U.S. Cl.
CPC ................. *C11B 3/006* (2013.01); *C07C 51/48* (2013.01); *C07C 51/50* (2013.01); *C11B 3/003* (2013.01)

(58) Field of Classification Search
CPC ........ C07C 51/487; C11B 3/001; C11B 3/06; C11C 1/103
USPC .......................................................... 554/194
See application file for complete search history.

(56) References Cited

FOREIGN PATENT DOCUMENTS

| EP | 0379963 A1 | * | 8/1990 |
| JP | 6248289 | * | 9/1994 |
| JP | 7242895 A | * | 9/1995 |
| JP | 2001240893 A | * | 9/2001 |
| WO | WO 2010029706 A1 | * | 3/2010 |
| WO | WO 2010/148046 | | 12/2010 |

OTHER PUBLICATIONS

Tao et al., "Study on Extracting High Contents of DHA and EPA by Using Nitrate-Water Method," *Chinese Journal of Marine Drugs*, No. 3, pp. 28-30 (Mar. 2004).
International Preliminary Report on Patentability for PCT/IB2011/002593, dated Mar. 26, 2013.
Written Opinion of the International Search Authority for PCT/IB2011/002593, dated Mar. 24, 2013.
International Search Report for PCT/IB2011/002593, dated Mar. 29, 2012.

* cited by examiner

*Primary Examiner* — Deborah D Carr
(74) *Attorney, Agent, or Firm* — Finnegan, Henderson, Farabow, Garrett & Dunner, L.L.P.

(57) ABSTRACT

The present disclosure relates generally to processes for concentrating omega-3 fatty acids from a fatty acid oil mixture with an aqueous silver salt, such as an aqueous $AgNO_3$ solution.

57 Claims, 5 Drawing Sheets

PROCESS FOR CONCENTRATING OMEGA-3 FATTY ACIDS

This application is a National Phase application based on International Patent Application No. PCT/IB2011/002503 filed on Sep. 23, 2011, and claims priority to U.S. Provisional Application No. 61/386,096, filed on Sep. 24, 2010, which are incorporated herein by reference in their entities.

The present disclosure relates generally to a process for concentrating polyunsaturated fatty acids, such as omega-3 fatty acids, from a fatty acid oil mixture with an aqueous silver salt solution, such as an aqueous $AgNO_3$ solution.

Omega-3 fatty acids are useful in a number of applications, including in pharmaceutical and/or nutritional supplement products. For example, omega-3 fatty acids may regulate plasma lipid levels, cardiovascular and immune functions, insulin action, neuronal development, and visual function. Omega-3 fatty acids may have beneficial effects on the risk factors for cardiovascular diseases, such as hypertension and hypertriglyceridemia, and on the coagulation factor VII phospholipid complex activity. Omega-3 fatty acids may also lower serum triglycerides, increase serum HDL cholesterol, lower systolic and diastolic blood pressure and/or pulse rate, and may lower the activity of the blood coagulation factor VII-phospholipid complex. Further, omega-3 fatty acids are generally well-tolerated, without giving rise to severe side effects.

Marine oils, also commonly referred to as fish oils, are a source of omega-3 fatty acids, including eicosapentaenoic acid (EPA) and docosahexaenoic acid (DHA), which have been found to regulate lipid metabolism. Plant-based oils, microbial oils, and algae oils are also sources of omega-3 fatty acids. Several formulations of omega-3 fatty acids have been developed. For example, one form of omega-3 fatty acid oil mixture is a concentrate of primary omega-3, long chain, polyunsaturated fatty acids from fish oil containing DHA and EPA, such as those sold under the trademark Omacor®/Lovaza™/Zodin®/Seacor®. See, for example, U.S. Pat. Nos. 5,502,077, 5,656,667, and 5,698,594. In particular, each 1000 mg capsule of Lovaza™ contains at least 90% omega-3 ethyl ester fatty acids (84% EPA/DHA); approximately 465 mg EPA ethyl ester and approximately 375 mg DHA ethyl ester.

Other omega-3 fatty acids may provide activity. For example, Kaur et al. (*Prog. Lipid Res.* (2011) vol. 50(1), pp. 28-34) attribute certain biological effects to n-3 DPA. There is evidence that n-3 DPA possesses 10-fold greater endothelial cell migration ability than EPA, which may be important in wound-healing processes. Additionally, n-3 DPA is reportedly more effective than EPA and DHA in inhibiting blood platelet aggregation. Further, n-3 DPA may play a role in attenuating age-related decrease in spatial learning and long-term potentiation. However, n-3 DPA has not been extensively studied because of the limited availability of the pure compound.

Many of the sources of omega-3 fatty acids also are sources of omega-6 fatty acids. In certain biological processes, however, omega-3 and omega-6 fatty acids may express opposite activities, such that low concentrations of omega-6 fatty acids are desired, i.e., high n-3/n-6 ratios. A commercial product that complies with Ph. Eur. Monograph 1250 typically has an n-3/n-6 ratio in the range of 24-40.

An overview of methods for preparing concentrates of omega-3 acids is given by Brevik (*Long-Chain Omega-3 Specialty Oils*, The Oily Press, PJ Barnes & Associates, Bridgwater UK, pp. 111-140, 2007). Because of the complex fatty acid compositions of marine oils, it is difficult to prepare highly concentrated compositions of omega-3 fatty acids using only one concentration technique. Normally, a combination of techniques is used, most often techniques that combine separation according to unsaturation (e.g., enzymatic separation and/or urea fractionation) with separation according to carbon chain length (e.g., molecular/short path distillation and/or supercritical fluid extraction). Conventional techniques often have the disadvantage of giving concentrates with low yields of omega-3 fatty acids compared to the amounts in the starting oil. This may be particularly problematic when combining low-yield techniques like urea fractionation and short path distillation.

Additionally, separation processes like short-path distillation and other processes that mainly separate fatty acid esters based on chain length typically do not separate between omega-3 and omega-6 fatty acids with the same number of carbon atoms, such as C20:4n-3 and C20:4n-6, or C22:5n-3 and C22:5n-6. Urea fractionation, for example, may result in higher concentration factors for omega-6 fatty acids than for the homologue omega-3 fatty acids since the tendency of a fatty acid derivative to form solid complexes with urea increases with the distance from the first double bond to the carbonyl group of the fatty acid ester (commonly known as the $\Delta$ value). If an omega-6 fatty acid has a $\Delta$ value of $\Delta'$, the corresponding omega-3 fatty acid has a $\Delta$ value of $(\Delta'+3)$, resulting in a higher degree of complex formation with urea. This tendency becomes especially pronounced for high concentrates of omega-3 fatty acids, where large relative amounts of urea are utilized.

Studies have been done using silver salts to isolate polyunsaturated fatty acids from a mixture. See, e.g., Quinn at al. (pp. 133-169 in Perry et al., *Progress in Separation and Purification* 4, Wiley-Interscience, New York, 1971); Peers et al. (*J. Food Technology* (1986) vol. 21 pp. 483-469); Suzuki et al. (*Bioseparation* (1993) vol. 3, pp. 197-204); Teramoto et al. (*Ind. Eng. Chem. Res.* (1994), vol. 33 pp. 341-345); Teramoto et al. (*J. Membrane Sci.*, (1994) vol. 91, pp. 209-213); Kubota et al. (*Sep. Sci. Technol.* (1997), vol. 32, pp. 1529-1541); Chen et al. (J. Jiangsu University of Science and Technology (*Natural Science*) (2000), vol. 21, pp. 18-22); Tao et al. (*Chinese J. Marine Drugs*, (2004) No. 3, pp. 28-30); Huong (*J. Chemistry* (2007), vol. 45, pp. 757-762); Li et al. (*Sep. Sci. Technol.* (2008) vol. 43, pp. 2072-2089); EP 0454430B1; EP 0576191A2; Seike et al. (Journal of Chemical Engineering of Japan (2007), Vol. 40, pp 1076-1084); and Kamio et al. (Ind. Eng. Chem. Res., (2011) vol. 50(11), pp. 6915-24). However, previously-known methods do not provide for a sufficiently selective and/or efficient process for concentrating omega-3 fatty acids.

Thus, there remains a need in the art for a more efficient process for concentrating omega-3 fatty acids from a fatty add oil mixture.

It is to be understood that both the foregoing general description and the following detailed description are exemplary and explanatory only and are not restrictive of the invention, as claimed.

The present disclosure generally relates to a process for concentrating at least one omega-3 fatty acid from a fatty acid oil mixture, the process comprising: (a) combining the fatty acid oil mixture and an aqueous silver salt (such as $AgNO_3$ or $AgBF_4$) solution to form an aqueous phase and an organic phase, wherein in the aqueous phase, the aqueous silver salt solution forms a complex with the at least one omega-3 fatty acid; (b) separating the aqueous phase from the organic phase; (c) extracting the aqueous phase with a displacement liquid, or increasing the temperature of the aqueous phase to at least 30° C., or a combination of extracting with a displacement liquid and increasing the temperature, resulting in formation of at least one extract; (d) combining the aqueous phase with water, or extracting the aqueous phase with supercritical $CO_2$, or a combination of combining the aqueous phase with water and extracting the aqueous phase with supercritical $CO_2$, to dissociate the complex, wherein an aqueous phase comprising the silver salt and at least one solution comprising a fatty acid concentrate forms; and (e) separating the at least one solution comprising the fatty acid concentrate from the aqueous phase comprising the silver salt.

DESCRIPTION

Figure 1:
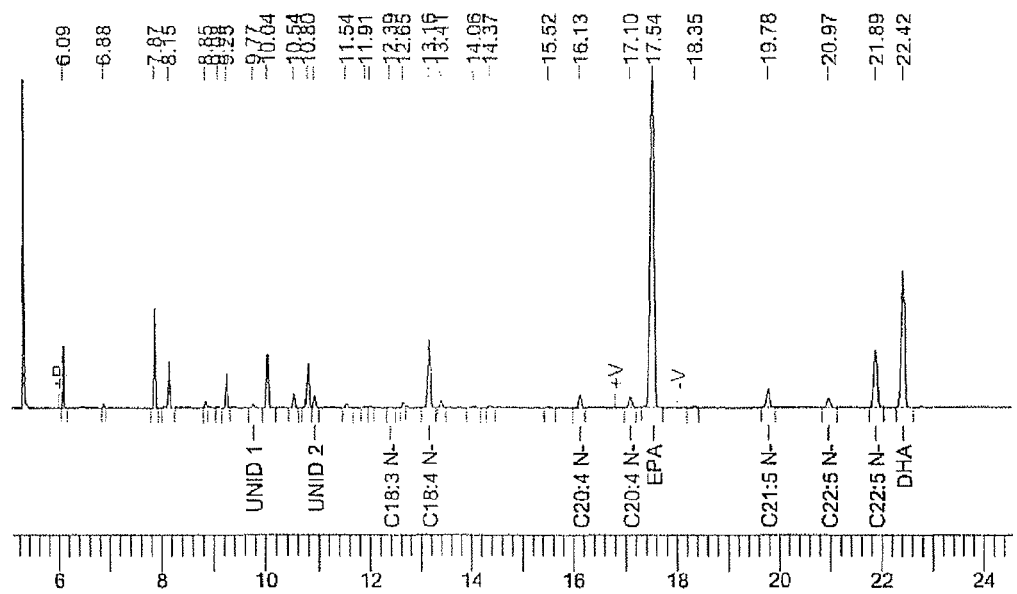
FIG. 1 is a gas chromatogram of the fatty acid concentrate recovered by heating the aqueous phase to 70° C., as described in Example 1.

Particular aspects of the disclosure are described in greater detail below. The terms and definitions as used in the present application and as clarified herein are intended to represent the meaning within the present disclosure. The patent and scientific literature referred to herein and referenced above is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass±30% of a specified amount, frequency or value.

The term "fatty acid(s)" includes, e.g., short-chain and long-chain saturated and unsaturated (e.g., monounsaturated and polyunsaturated) hydrocarbons comprising at least one carboxylic acid group.

The term "omega-3 fatty acid(s)" includes natural and synthetic omega-3 fatty acids, as well as pharmaceutically-acceptable esters, free acids, triglycerides, derivatives, conjugates (see, e.g., Zaloga at al., U.S. Publication No. 2004/0254357, and Horrobin et al., U.S. Pat. No. 6,245,811, each hereby incorporated by reference), precursors, salts, and mixtures thereof. Examples of omega-3 fatty acid oils include, but are not limited to, omega-3 polyunsaturated fatty acids such as α-linolenic acid (ALA, 18:3n-3), octadecatetraenoic acid (i.e., stearidonic acid, STA, 18:4n-3), eicosatrienoic acid (ETE, 20:3n-3), eicosatetraenoic acid (ETA, 20:4n-3), eicosapentaenoic acid (EPA, 20:5n-3), heneicosapentaenoic acid (HPA, 21:5n-3), docosapentaenoic acid (DPA, clupanodonic acid, 22:5n-3), and docosahexaenoic acid (DHA, 22:6n-3); esters of omega-3 fatty acids with glycerol such as mono-, di- and triglycerides; and esters of the omega-3 fatty acids and a primary, secondary, and/or tertiary alcohol, such as, for example, fatty acid methyl esters and fatty acid ethyl esters.

The term "omega-6 fatty acid(s)" includes natural and synthetic omega-6 fatty acids, as well as pharmaceutically-acceptable esters, free acids, triglycerides, derivatives, conjugates, precursors, salts, and mixtures thereof. Examples of omega-6 fatty acid oils include, but are not limited to, omega-6 polyunsaturated, long-chain fatty acids such as linoleic acid (18:2n-6), γ-linolenic acid (18:3n-6), eicosadienoic acid (20:2n-6), dihomo-γ-linolenic acid (20:3n-6), arachidonic acid (20:4n-6), docosadienoic acid (22:2n-6), adrenic acid (22:4n-6), and docosapentaenoic acid (i.e., osbond acid, 22:5n-6); and esters, triglycerides, derivatives, conjugates, precursors, salts, and/or mixtures thereof.

The polyunsaturated fatty acids (e.g., omega-3 fatty acids and/or omega-6 fatty acids), esters, triglycerides, derivatives, conjugates, precursors, salts and/or mixtures thereof according to the present disclosure can be used in their concentrated and/or purified form and/or as a component of an oil, for example, as marine oil (e.g., fish oil), algae oils, microbial oils, and/or plant-based oils.

Fatty Acid Oil Mixture

The fatty acid oil mixture according to the present disclosure may be derived from animal oil(s) and/or non-animal oil(s). In some embodiments of the present disclosure, the fatty acid oil mixture is derived from at least one oil chosen from marine oil, single cell oils, algae oil, plant-based oil, microbial oil, and combinations thereof. Marine oils include, for example, fish oil, krill oil, and lipid composition derived from fish. Plant-based oils include, for example, flaxseed oil, canola oil, mustard seed oil, and soybean oil. Single cell/microbial oils include, for example, products by Martek, Nutrinova, and Nagase & Co. Single cell oils are often defined as oils derived from microbial cells and which are destined for human consumption. See, e.g., Wynn and Ratledge, "Microbial oils: production, processing and markets for specialty long-chain omega-3 polyunsatutrated fatty acids," pp. 43-76 in Breivik (Ed.), *Long-Chain Omega-3 Specialty Oils*, The Oily Press, P.J. Barnes & Associates, Bridgewater UK, 2007.

Additional oils include triglyceride vegetable oils, commonly known as long chain triglycerides such as castor oil, corn oil, cottonseed oil, olive oil, peanut oil, safflower oil, sesame oil, soybean oil, hydrogenated soybean oil, and hydrogenated vegetable oils; medium chain triglycerides such as those derived from coconut oil or palm seed oil, monoglycerides, diglycerides, and triglycerides. In addition to mixed glycerides, there are other oils such as esters of propylene glycol such as mixed diesters of caprylic/capric acids of propylene glycol, esters of saturated coconut and palm kernel oil-derived caprylic, linoleic, succinic, or capric fatty acids of propylene glycol.

The fatty acids of the fatty acid oil mixture may be esterified, such as alkyl esters, for example ethyl esters. In some embodiments, the fatty acids are in glyceride form, such as chosen from mono-, di-, and triglycerides. In other embodiments, the fatty acids are in free acid form.

Unsaturated fatty acids of the fatty acid oil mixture may be in cis and/or trans configuration. Examples of omega-3 fatty acids in all-cis configuration include, but are not limited to, (all-Z)-9,12,15-octadecatrienoic acid (ALA), (all-Z)-6,9,12,15-octadecatetraenoic acid (STA), (all-Z)-11,14,17-eicosatrienoic acid (ETE), (all-Z)-8,11,14,17-elcosatetraenoic acid (ETA), (all-Z)-,7,10,13,16,19-docosapentaenoic acid (DPA), (all-Z)-5,8,11,14,17-eicosapentaenoic acid (EPA), (all-Z)-4,7,10,13,16,19-docosahexaenoic acid (DHA), and (all-Z)-6,9, 12,15,18-heneicosapentaenoic acid (HPA). Examples of omega-6 fatty acids in all-cis configuration include, but are not limited to, (all-Z)-4,7,10,13,16-docosapentaenoic acid (osbond acid), (all-Z)-9,12-octadecadienoic acid (linoleic acid), (all-Z)-5,8,11,14-eicosatetraenoic acid (AA), and (all-Z)-6,9,12-octadecatrienoic acid (GLA). Examples of monounsaturated fatty acids in cis configuration include, but are not limited to, (Z)-9-hexadecenoic acid (palmitoleic acid), (Z)-9-octadecenoic acid (oleic acid), (Z)-11-octadecenoic acid (vaccenic acid), (Z)-9-eicosenoic acid (gadoleic acid), (Z)-11-elcosenoic acid (gondoic acid), (Z)-11-eicoesenoic acid, (Z)-11-docosenoic acid (cetoleic acid), Z-13-docosenolc acid (erucic acid), and (R-(Z))-12-hydroxy-9-octadecenoic acid (ricinoleic acid).

Examples of fatty acid oil mixtures according to the present disclosure include, but are not limited to, the fatty acids defined in the European Pharmacopoeia Omega-3 Acid Ethyl Esters 60, the European Pharmacopoeia Fish Oil Rich in Omega-3 Acids Monograph, the USP Fish Oil Monograph, the European Pharmacopoeia Omega-3 Acid Triglycerides, the European Pharmacopoeia Omega-3-Acid Ethyl Esters 90, and the USP Omega-3-Acid Ethyl Esters monograph.

Commercial examples of fatty acid oil mixtures comprising different fatty acids include, but are not limited to: Incromega™ omega-3 marine oil concentrates such as Incromega™ TG7010 SR, Incromega™ E7010 SR, Incromega™ TG6015, Incromega™ EPA500TG SR, Incromega™ E400200 SR, Incromega™ E4010, Incromega™ DHA700TG SR, Incromega™ DHA700E SR, Incromega™ DHA500TG SR, Incromega™ TG3322 SR, Incromega™ E3322 SR, Incromega™ TG3322, Incromega™ E3322, Incromega™ Trio TG/EE (Croda International PLC, Yorkshire, England); EPAX6000FA, EPAX5000TG, EPAX4510TG, EPAX2050TG, EPAX5500EE, EPAX5500TG, EPAX5000EE, EPAX5000TG, EPAX6000EE, EPAX6000TG, EPAX6500EE, EPAX6500TG, EPAX1050TG, EPAX2050TG, EPAX6015TG/EE, EPAX4020TG, and EPAX4020EE (EPAX is a wholly-owned subsidiary of Trygg Pharma AS; Omacor®/Lovaza™/Zodin®/Seacor® finished pharmaceutical product, K85EE, AGP 103, K30EE, K50EE, and K70EE (Pronova BioPharma Norge AS); MEG-3® EPA/DHA fish oil concentrates (Ocean Nutrition Canada); DHA FNO "Functional Nutritional Oil" and DHA CL "Clear Liquid" (Lonza); Superba™ Krill Oil (Aker Biomarine); omega-3 products comprising DHA produced by Martek; Neptune krill oil (Neptune); cod-liver oil products and anti-reflux fish oil concentrate (TG) produced by Mellers; Lysi Omega-3 Fish oil; Seven Seas Triomega® Cod Liver Oil Blend (Seven Seas); Fri Flyt Omega-3 (Vesterålens); and Epadel (Mochida). Those commercial embodiments provide for various omega-3 fatty acids, combinations, and other components as a result of the transesterification process or method of preparation in order to obtain the omega-3 fatty acid(s) from various sources, such as marine, algae, microbial (single cell), and/or plant-based sources.

In some embodiments of the present disclosure, the fatty acid oil mixture comprises at least one omega-3 fatty acid, such as EPA and/or DHA. In at least one embodiment, the fatty acid oil mixture comprises EPA and DHA. The fatty acid oil mixture may further comprise at least one other fatty acid, for example a polyunsaturated fatty acid (PUFA) other than EPA and DHA. Examples of such PUFAs include, but are not limited to, other omega-3 fatty acids, such as $C_{20}$-$C_{22}$ omega-3 fatty acids other than EPA and DHA, and omega-6 fatty acids.

In some embodiments of the present disclosure, the process produces concentrates of C22:5n-3 (n-3 DPA).

Process for Concentrating Omega-3 Fatty Acid(s)

Some embodiments of the present disclosure relate to a process for concentrating at least one omega-3 fatty acid from a fatty acid oil mixture.

According to one embodiment, the process comprises combining a fatty acid oil mixture with an aqueous silver salt solution, such as silver nitrate ($AgNO_3$) solution. Although the present discussion focuses on $AgNO_3$, one of ordinary skill in the art would recognize that other suitable silver salts may be used, such as silver tetrafluoroborate ($AgBF_4$). Silver ions may form a complex with polyunsaturated fatty acids in the fatty acid oil mixture, such as omega-3 fatty acids, for example EPA and/or DHA. The silver complex(es) thus formed may remain in the aqueous phase while other fatty acids present in the fatty acid oil mixture (e.g., saturated fatty acids, short-chain fatty acids, monounsaturated fatty acids, and/or other unsaturated fatty acids such as fatty acids with fewer double bonds than the complexed PUFA), may remain in the organic phase as undissolved fatty acids.

The concentration of the silver salt solution, e.g., $AgNO_3$ solution, may range from about 10% wt. to about 90% wt, such as from about 60% wt. to about 80% wt. In some embodiments, for example, the concentration of aqueous $AgNO_3$ solution is about 60% wt., about 70% wt., about 75% wt., or about 80% wt. In some embodiments, the weight ratio of fatty acid oil mixture to $AgNO_3$(s) is at least 0.4. For example, in some embodiments, the weight ratio of fatty acid oil mixture to $AgNO_3$ ranges from about 0.4 to about 1.6. The fatty acid oil mixture and $AgNO_3$ solution may be combined at room temperature (e.g., from about 20° C. to about 25° C.), or at a temperature below room temperature by cooling, for example from about −25° C. to about 20° C., or at a temperature above room temperature, for example from about 25° C. to about 90° C.

At least one organic solvent, such as a polar organic solvent, may be added to the $AgNO_3$ solution before and/or after mixing with the fatty acid oil mixture. Examples of suitable organic solvents include, but are not limited to, alcohols such as ethanol and methanol. Addition of a polar organic solvent may, for example, enhance the solubility of fatty acids from the fatty acid oil mixture into the aqueous $AgNO_3$ solution.

The fatty acid oil mixture and $AgNO_3$ solution are generally mixed on the order of minutes to several hours, for example, from about 15 minutes to about two hours, resulting in an organic phase and an aqueous phase, such as an oil-water emulsion. The skilled person will realize that the mixing time required will depend on the volumes involved and the efficiency of mixing. For example, in a slug flow prepared by a microreactor, less than 20 s may be required to reach equilibrium when extracting DHA ethyl ester and EPA ethyl ester with aqueous silver nitrate solution (Seike et al. (2007) Journal of Chemical Engineering of Japan, Vol. 40, pp 1076-1084). For large volumes that are brought together with less efficient mixing, the transfer and complexation of fatty acids with the aqueous silver ion solution will take a substantially longer time to reach equilibrium, for example 2 or more hours.

Upon settling, the organic phase and aqueous phase may be separated according to methods known in the art. Phase separation may, for example, take place by allowing the mixture to stand for a sufficient amount of time to obtain two substantially transparent phases, by centrifugation, by membrane technology, or by other suitable means.

After removing the organic phase, the aqueous phase may be extracted with a displacement liquid, such as an organic solvent, resulting in formation of at least one extract. The displacement liquid may, for example, provide for enhanced selectivity by preferentially removing certain fatty acids such as omega-6 fatty acids and/or omega-3 fatty acids other than EPA and DHA. Without being bound by theory, the displacement liquid may provide selectivity by affecting the relative solubility of fatty acids in the aqueous phase and/or through interactions with the silver complexes. In some instances, the displacement liquid may be selected such that it does not form a complex with silver ions, or such that it forms a weaker complex with silver ions than the omega-3 fatty acid to be concentrated. Examples of suitable displacement liquids include, but are not limited to, alkanes, alkenes, cycloalkanes, cycloalkenes, dienes, aromates, and halogenated solvents. Non-limiting mention may be made of specific examples, such as dichloromethane and other solvents containing one or more chlorine atoms and/or one or more of other halides, hexane, hexene, heptane, heptene, cyclohexane, cyclohexene, 1,7-octadiene, 1,5-cyclooctadiene, as well as other alkenes comprising one or more double bonds, such as alkenes comprising one, two, or even three double bonds, and oxygen- and nitrogen-containing solvents such as ketones and amides/amines. The aqueous phase may be extracted more than once, i.e., at least two successive extractions. The amount of displacement liquid for each extraction may range from about 0.1 to about 5 times by weight the amount of fatty acid oil mixture that is dissolved in the aqueous silver ion phase.

Different displacement liquids and/or combinations of displacement liquids may be used according to the selectivity desired in concentrating one or more specific omega-3 fatty acids.

The aqueous phase and organic phase may be heated before they are separated. In such cases, the boiling point of the organic phase may be considered in determining the appropriate temperature. Generally speaking, the aqueous phase/organic phase mixture may be heated to a temperature ranging from about 30° C. to about 90° C.

In some embodiments, the aqueous phase is heated after removing the organic phase, resulting in formation of at least one extract. For example, the aqueous phase may be heated to a temperature of at least 30° C., such as a temperature ranging from about 30° C. to about 90° C. In such cases, heating may cause the release of a fatty acid oil mixture concentrated in omega-6 fatty acids and/or specific omega-3 fatty acids, such as $C_{20}$-$C_{22}$ omega-3 fatty acids other than EPA and DHA, from the aqueous phase. Heating should be done carefully in the absence of oxygen and at sufficiently mild conditions to avoid oxidation, isomerization and/or degradation of the polyunsaturated fatty acids.

Further according to the process, the aqueous phase may be diluted with water in order to dissociate $AgNO_3$ complex(es), thereby releasing a fatty acid concentrate, i.e., a fatty acid oil mixture concentrated in at least one omega-3 fatty acid. In some embodiments, the aqueous phase is diluted more than once, i.e., at least two successive dilutions. The amount of water used in dilution may range from about 1 to about 20 times the weight of solid silver nitrate ($AgNO_3$(s)) used. The exact amounts depend on a number of factors, including the silver ion concentration and the nature of the fatty acid oil mixture. The fatty acid concentrate may then be separated from the aqueous phase to form at least one solution. In some embodiments, the silver ions may be recovered for re-use in a subsequent process. For example, silver ions may be recovered for re-use by regeneration (including, e.g., regeneration via electrolysis), filtration, centrifugation, and/or purification.

Further according to the process, the aqueous phase may be extracted with carbon dioxide ($CO_2$) under supercritical pressure in order to dissociate $Ag^+$ complex(es), thereby releasing all or a fraction of the fatty acid concentrate. The carbon dioxide may contain at least one polar modifier such as water or an alcohol, for example ethanol. The benefits of extraction with carbon dioxide may include eliminating the need for large amounts of water for breaking the complex. The $CO_2$ is easily removed from the ethyl esters by releasing the pressure. $CO_2$ is non-toxic and may provide the inert atmosphere needed to protect the active $Ag^+$ from forming inactive $Ag_2O$.

The process according to the present disclosure may concentrate at least one omega-3 fatty acid while reducing the concentration of at least one omega-6 fatty acid in the fatty acid oil mixture. The process may, for example, increase the ratio of omega-3 to omega-6 fatty acids in the fatty acid concentrate relative to the fatty acid oil mixture. In some embodiments, the ratio of omega-3 fatty acids to omega-6 fatty acids (n-3/n-6) in the fatty acid concentrate mixture is greater than about 40, such as greater than about 80, greater than about 100, greater than about 150, or greater than about 200. In some embodiments, the total concentration of omega-6 fatty acids in the fatty acid concentrate may be less than about 3% by weight, such as less than about 2% by weight, or less than about 1% by weight.

The process presently disclosed may also concentrate one or more omega-3 fatty acids while reducing the concentration of other omega-3 fatty acids. In some embodiments, for example, the process concentrates EPA and DHA while reducing the concentration of $C_{20}$-$C_{22}$ omega-3 fatty acids other than EPA and DHA. In some embodiments, the total concentration of $C_{20}$-$C_{22}$ omega-3 fatty acids other than EPA and DHA in the fatty acid concentrate is less than 3% by weight, such as less than 2.5% by weight, such as less than 0.5% by weight.

The process presently disclosed further provides for adjusting the EPA/DHA ratio in a fatty acid oil mixture by concentrating one omega-3 fatty acid relatively more or less in comparison to the other omega-3 fatty acid. For example, the EPA/DHA ratio may be adjusted by varying temperature, displacement liquid, and/or water dilution ratio, and by extracting with $CO_2$ with or without a polar modifier, such as water or an alcohol, for example ethanol. In some embodiments, the EPA/DHA ratio in at least one of the fatty acid concentrate, at least one extract, and at least one solution ranges from about 0.1 to about 10 by weight.

The fatty acid concentrate, at least one extract, and/or at least one solution may be purified by using at least one purification process. The purification process may remove, for example, residual silver compounds, residual displacement liquid, lower-chain fatty acids (e.g., fatty acid 16:4n-1), lower molecular weight compounds enriched by complexation with silver ions, environmental pollutants, cholesterol, and/or vitamins. Such purification processes include, but are not limited to, short-path distillation, molecular distillation, supercritical fluid extraction, enzymatic separation processes, iodolactonization fractionation, and preparative chromatography.

The process presently disclosed may be repeated to further concentrate the at least one omega-3 fatty acid and/or to concentrate one or more other omega-3 fatty acids. The process may also be used to concentrate at least one omega-6 fatty acid. For example, the fatty acid concentrate, at least one extract and/or at least one solution may comprise the fatty acid oil mixture in one or more subsequent processes as described above. The fatty acid concentrate obtained from one or more concentration processes according to the present disclosure may comprise at least 80% of at least one omega-3 fatty acid, such as at least 90%, at least 95%, or even at least 98% of at least one omega-3 fatty acid.

The fatty acid concentrate, at least one extract, and/or at least one solution obtained from the process presently disclosed may also be treated by at least one conventional fractionation process such as short-path distillation, molecular distillation, iodolactonization fractionation, enzymatic fractionation processes, extraction, and/or chromatography. The fatty acid concentrate thus obtained may comprise at least 80% of at least one omega-3 fatty acid, such as at least 90%, at least 95%, or even at least 98% of at least one omega-3 fatty acid. In one embodiment, for example, the at least one fractionation process produces a fatty acid concentrate comprising at least 90% (all-Z)-4,7,10,13,16,19-docosahexaenoic acid (DHA), such as at least 95% DHA, or for example, at least 98% DHA. In another embodiment, the at least one fractionation process produces a fatty acid concentrate comprising at least 80% (all-Z)-7,10,13,16,19-docosapentaenoic acid (DPA), such as at least 90% DPA, such as at least 95% DPA, or for example, at least 98% DPA. A person of ordinary skill in the art will recognize that treating concentrates obtained according to the present disclosure by at least one conventional fractionation process can produce compositions that comply with, for example, the European Pharmacopoeia Monograph 1250, Omega-3-Acid Ethyl Esters 90 monograph, and/or the USP Omega-3-Acid Ethyl Esters monograph.

The process presently disclosed may reduce the concentration of at least one environmental pollutant in the fatty acid oil mixture, such that the fatty acid oil concentrate, the at least one extract, and/or at least one solution comprises a lower concentration of the at least one environmental pollutant than the fatty acid oil mixture. Environmental pollutants include, but are not limited to, polychlorinated biphenyl (PCB) compounds, polychlorinated dibenzodioxin (PCDD) compounds, polychlorinated dibenzofuran (PCDF) compounds, brominated flame retardants like polybrominated diphenyl ethers (PBDE), tetrabromobisphenol A (TBBP-A) and hexabromocyclododecane (HBCD), and pesticides like DDT (2,2 bis-(p-chlorophenyl)-1,1,1-trichloroethane) and metabolites of DDT. The process presently disclosed may also reduce the concentration of total cholesterol (i.e., free and/or bound cholesterol) in the fatty acid oil mixture, such that the fatty acid concentrate comprises a lower concentration of total cholesterol than the fatty acid oil mixture. In some embodiments of the present disclosure, the fatty acid oil mixture is stripped in at least one stripping processing step, e.g., distillation, before combining with the aqueous $AgNO_3$ solution, wherein the stripping processing step decreases the amount of at least one environmental pollutant and/or total cholesterol in the fatty acid oil mixture.

The following examples are intended to illustrate the present disclosure without, however, being limiting in nature. It is understood that the skilled artisan will envision additional embodiments consistent with the disclosure provided herein. The composition values given in the following tables are based on gas chromatography (GC) area percentages. A person of ordinary skill in the art will understand that GC area percentages differ from GC mass percentages, e.g., they may be higher than the corresponding GC mass percentages. A procedure for analyzing GC mass percentages is provided in the European Pharmacopoeia Monograph 2.4.29, Composition of Fatty Acids in Oils Rich in Omega-3-Acids.

EXAMPLES

Example 1

Temperature

Before Phase Separation. K50EE was mixed with 70% wt. $AgNO_3$ solution (K50EE:$AgNO_3$=3:5) for about 1.5 hours and brought to the desired temperature (see Table 1, i.e., 8° C., 21° C., 50° C., 60° C., or 70° C.). The oil/water mixture was left to stand for about 2 hours to separate into an aqueous phase and organic phase, and the organic phase was removed. The aqueous phase was diluted in water (water:$AgNO_3$(s), about 7.5:1 by weight) causing the release of organic material, i.e., a fatty acid concentrate. The concentrate was collected and its composition determined by GC analysis (GC area %) as shown in Table 1. The results show that higher temperatures reduced the relative concentration of n-6 fatty acid and/or specific n-3 fatty acids (e.g., long-chain (LC) fatty acids other than EPA and DHA).

TABLE 1

Composition of fatty acid concentrates; K50EE:$AgNO_3$ = 3:5 mixed at various temperatures (GC area %).

| Fatty acid ethyl ester | K50EE | 8° C. | 21° C. | 50° C. (I) | 50° C. (II) | 60° C. | 70° C. |
| --- | --- | --- | --- | --- | --- | --- | --- |
| 18:2n-6 | 1.14 | 0.27 | 0.26 | 0.08 | ** | 0.03 | 0.05 |
| 18:3n-3 | 0.62 | 0.26 | 0.21 | 0.11 | 0.07 | 0.07 | 0.05 |
| 18:4n-3 | 1.78 | 2.08 | 1.92 | 1.76 | 1.80 | 1.71 | 1.48 |
| 20:4n-6 | 1.66 | 1.01 | 0.84 | 0.48 | 0.45 | 0.40 | 0.30 |
| 20:4n-3 | 1.19 | 1.08 | 0.90 | 0.62 | 0.59 | 0.54 | 0.43 |
| EPA | 32.80 | 44.53 | 44.31 | 45.87 | 46.57 | 46.08 | 44.61 |
| 21:5n-3 | 1.32 | 1.96 | 1.77 | 1.72 | 1.74 | 1.68 | 1.55 |
| 22:5n-6 | 0.62 | 0.65 | 0.54 | 0.40 | 0.37 | 0.33 | 0.25 |
| 22:5n-3 | 4.64 | 6.64 | 5.71 | 5.07 | 4.98 | 4.67 | 4.08 |
| DHA | 25.48 | 34.72 | 36.69 | 41.31 | 41.66 | 42.50 | 44.80 |
| EPA + DHA | 58.28 | 79.25 | 81.00 | 87.18 | 88.23 | 88.58 | 89.41 |
| Σn-3 | 70.83 | 91.27 | 91.51 | 96.46 | 97.41 | 97.25 | 97.00 |
| Σn-6 | 3.42 | 1.93 | 1.64 | 0.96 | 0.82 | 0.76 | 0.60 |
| Σn-3/Σn-6 | 20.7 | 47.2 | 55.8 | 100 | 119 | 128 | 162 |

** GC area of 0.02% or below.

After Phase Separation. K30EE was stirred with 70% wt. $AgNO_3$ solution (K30EE:$AgNO_3$=1.2:1) at room temperature and allowed to separate into the aqueous phase and organic phase. The organic phase was removed. The aqueous phase was then heated to 70° C., causing the release of a fatty acid concentrate ("Concentrate-1") enriched in n-6 fatty acids and specific n-3 fatty acids, compared to a concentrate prepared using the same procedure as in this example, but without heating ("Concentrate ambient"). The aqueous phase was diluted in water (water:$AgNO_3$(s)=about 7.5:1 by weight) to obtain a second concentrate ("Concentrate-2") with an increased n-3/n-6 ratio and lower concentration of n-3 fatty acids other than EPA and DHA compared to the first concentrate. See Table 2.

TABLE 2

Composition of fatty acid concentrates; aqueous phase heated to 70° C.

| Fatty acid ethyl ester | K30EE | Concentrate ambient | Concentrate-1 | Concentrate-2 |
| --- | --- | --- | --- | --- |
| 16:4n-1 | 1.24 | 5.07 | 3.57 | 6.74 |
| 18:1n-9 | 11.94 | 0.73 | 3.20 | — |

TABLE 2-continued

Composition of fatty acid concentrates; aqueous phase heated to 70° C.

| Fatty acid ethyl ester | K30EE | Concentrate ambient | Concentrate-1 | Concentrate-2 |
|---|---|---|---|---|
| 18:3n-3 | 0.59 | 0.07 | 0.37 | — |
| 18:4n-3 | 2.15 | 3.31 | 5.75 | 2.81 |
| 20:4n-6 | 1.03 | 0.33 | 1.29 | 0.13 |
| 20:4n-3 | 0.50 | 0.37 | 1.66 | 0.20 |
| EPA | 18.51 | 45.36 | 42.68 | 45.67 |
| 21:5n-3 | 0.71 | 1.57 | 1.96 | 1.44 |
| 22:5n-6 | 0.3* | 0.35 | 1.01 | 0.21 |
| 22:5n-3 | 2.29 | 3.69 | 6.58 | 2.94 |
| DHA | 12.21 | 34.81 | 15.75 | 38.51 |
| EPA + DHA | 30.72 | 80.17 | 58.43 | 84.18 |
| Σn-3 | 36.96 | 89.18 | 74.75 | 91.57 |
| Σn-6 | 1.3 | 0.68 | 2.30 | 0.34 |
| Σn-3/Σn-6 | 28 | 131 | 32.5 | 269 |

*Estimated from peak size

Figure 2:
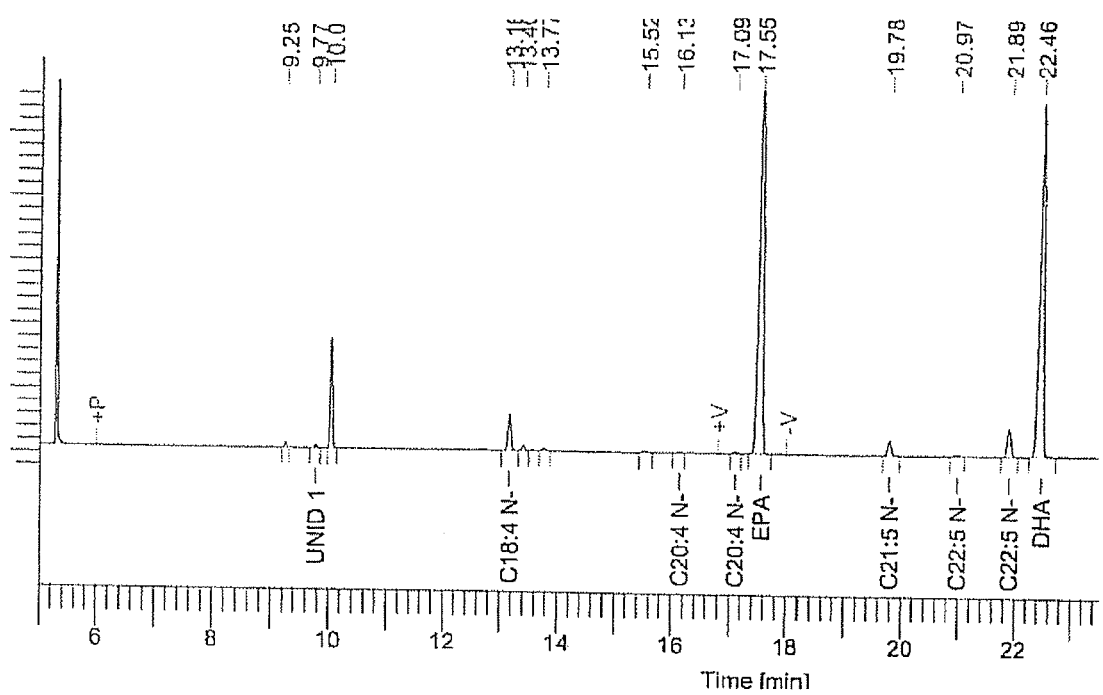
FIG. 2 is a gas chromatogram of the fatty acid concentrate obtained by diluting the aqueous phase in water after removing the concentrate shown in FIG. 1, as described in Example 1.

FIGS. 1 and 2 show the gas chromatographs for Concentrate-1 and Concentrate-2, respectively. Comparison of FIGS. 1 and 2 indicates that the process presently disclosed selectively removes fatty acid compounds to give a concentrate (e.g., FIG. 2) with lower amounts of specific fatty acids as compared to the starting mixture.

The high salt concentration of the aqueous phase reduces the melting point so that separation processes similar to those described above can be performed at temperatures well below 0° C. Possibly also the content of polyunsaturated fatty acids/fatty acid derivatives in the aqueous phase will result in an even further reduction of melting point. When working with the process disclosed herein, experiments have for example been performed with 70% aqueous silver nitrate solution at −20° C. without any solidification or partial solidification of the aqueous phase taking place. Probably the temperatures could be reduced even further. The skilled person will realize that such temperature reductions may increase the technical value of temperature modulation processes as discussed above.

It has been recognized in the art that low temperatures will facilitate the uptake of EPA and DHA ethyl esters (Seike et al. (2007) Journal of Chemical Engineering of Japan, Vol. 40, pp 1076-1084). However, it has not been appreciated in the art that temperature modulation can be utilized to separate fatty acid derivatives as illustrated by Table 2, for example to alter the n3/n6 ratio, to make intermediates suitable as starting materials for isolation of other fatty acids than EPA and DHA (for example, 22:5n-3), and to make concentrates of EPA and DHA that contain lower amounts of other long-chain omega-3 fatty acids.

Example 2A

Extraction with Displacement Liquid

K30EE was stirred with 70% wt. AgNO$_3$ solution (K30EE: AgNO$_3$(s)=1.2:1) at ambient temperature. The mixture was allowed to settle and the organic phase was removed. The aqueous phase was extracted with 1-hexene (hexene: AgNO$_3$(s)=about 0.54:1 by weight), then diluted in water (water:AgNO$_3$(s)=about 7.5:1 by weight). The fatty acid concentrate released by the dilution was collected and analyzed by GC. See Table 3.

TABLE 3

Composition of fatty acid concentrate; hexene extraction.

| Fatty acid ethyl ester | Concentration (GC area %) |
|---|---|
| 16:4n-1 | 5.21 |
| 18:3n-3 | ** |
| 18:4n-3 | 0.22 |
| 20:4n-6 | ** |
| 20:4n-3 | 0.02 |
| EPA | 40.14 |
| 21:5n-3 | 1.04 |
| 22:5n-6 | ** |
| 22:5n-3 | 1.37 |
| DHA | 50.16 |
| EPA + DHA | 90.30 |
| Σn-3 | 92.95 |
| Σn-6 | ** |
| Σn-3/Σn-6 | ∞‡ |
| Σ"Other C20-C22 n-3" | 2.43 |

**GC area of 0.02% or below.

‡Only peaks with area above 0.05% included.

Table 4A shows a comparison of different displacement liquids: the organic solvents hexane, 1-hexene, and cyclohexene. The following procedure was followed for all three solvents. Approximately 30.2 g of AgNO$_3$ was dissolved in 12.9 g water to prepare a 70% wt. AgNO$_3$ solution. The solution was stirred with approximately 24.1 g K30EE at 70° C. Phase separation was allowed to occur at 70° C., and the organic phase (about 17.1 g to 17.7 g) was removed. The aqueous phase was then extracted with four volumes of solvent (4×15.8 ml hexane, 4×16.1 ml hexene, 4×19.5 ml cyclohexene, respectively). The combination of the four extracts represents the "extract" for each solvent shown in Table 4A. The remaining aqueous phase was diluted with 225 ml water and allowed to stand overnight at room temperature in the dark. The fatty acid concentrate recovered from the aqueous phase was separated, and represents the "concentrate" for each solvent shown in Table 4A. Compositions are reported in GC area %.

Figure 3:
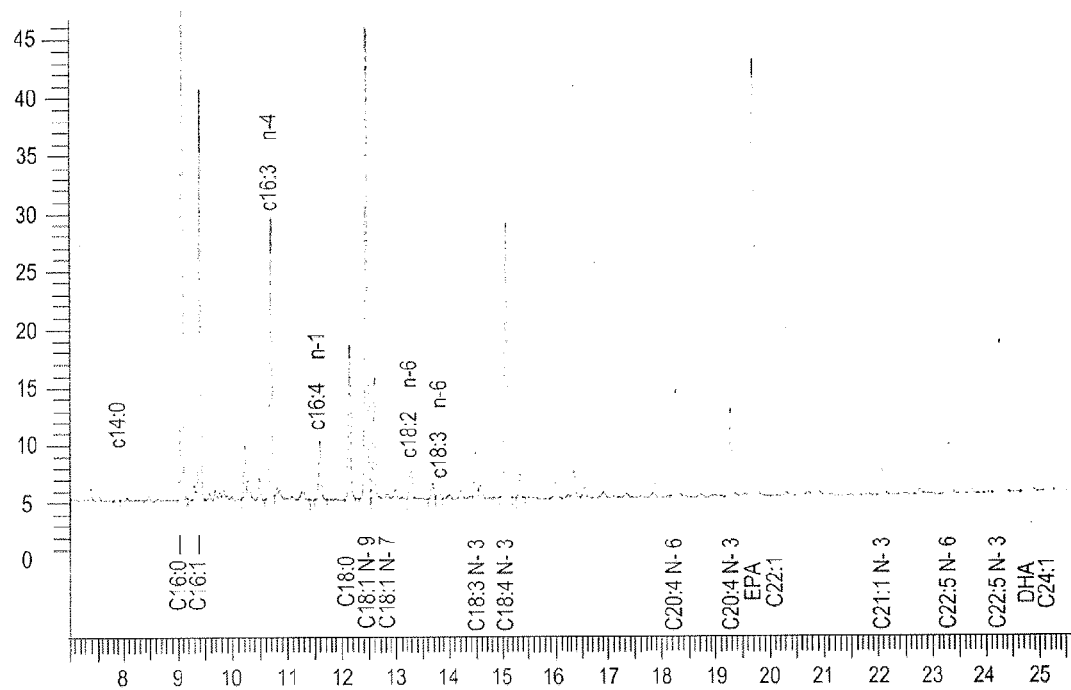
FIG. 3 is a gas chromatogram of a fraction obtained by extraction with hexane as a displacement solvent, as described in Example 2A at Table 4A.

A GC chromatogram of the extract produced by hexane is shown in FIG. 3. As can be seen from the GC areas as given in Table 4A, for example, the ratio DPAn-3/DHA is about 3.3:1, and the ratio DPAn-3/DPAn-6 is about 3.0:1 for the extract produced by hexane. Here, the so-called "Iodolactonization reaction" (see Breivik 2007) can be used to separate polyunsaturated fatty acids. By adding suitable amounts of reagents, the more stable five-ring iodo-γ-lactones of DHA and DPAn-6 will form, while DPAn-3 will remain substantially unaffected. The iodolactones of DHA and DPAn-6 can be removed from the unreacted fatty acids. In a fatty acid composition similar to that of FIG. 3, the iodolactonization reaction can be utilized to manufacture a fatty acid composition that substantially contains DPAn-3 (22:5n-3) as the only fatty acid with chain length of 22 carbon atoms. The skilled person will realize that such a product will be uniquely suited for production of pure DPAn-3.

TABLE 4A

Composition of fatty acid concentrates; displacement liquids hexane, 1-hexene, cyclohexene. K30EE was from the same batch as in Table 2.

| K30EE Fatty acid ethyl ester | Hexane | | 1-Hexene | | Cyclohexene | |
|---|---|---|---|---|---|---|
| | Extract | Concentrate | Extract | Concentrate | Extract | Concentrate |
| 16:4n-1 | 1.398 | 4.393 | 4.636 | 4.679 | 4.886 | 5.167 |
| 18:3n-3 | 1.019 | ** | 0.297 | ** | 0.167 | ** |
| 18:4n-3 | 7.608 | 1.905 | 9.824 | 1.792 | 6.584 | 0.936 |
| 20:4n-6 | 3.242 | ** | 1.782 | ** | 0.735 | ** |
| 20:4n-3 | 2.801 | ** | 1.813 | ** | 0.854 | ** |
| 20:5n-3 (EPA) | 13.43 | 47.316 | 42.263 | 46.44 | 53.469 | 40.536 |
| 21:5n-3 | 0.857 | 1.547 | 2.12 | 1.522 | 2.327 | 1.117 |
| 22:5n-6 | 1.734 | 0.136 | 1.435 | 0.174 | 0.841 | |
| 22:5n-3 | 5.288 | 2.961 | 8.818 | 2.979 | 7.069 | 1.583 |
| 22:6n-3 (DHA) | 1.603 | 40.755 | 6.82 | 41.51 | 14.595 | 50.441 |
| EPA + DHA | 15.033 | 88.071 | 49.083 | 87.95 | 68.064 | 90.977 |
| Σ n-3 | 32.606 | 94.484 | 71.955 | 94.243 | 85.065 | 94.613 |
| Σ n-6 | 4.976 | 0.136 | 3.217 | 0.174 | 1.576 | 0 |
| Σ n-3/n-6 | 6.6 | 694 | 22 | 541 | 53 | ∞‡ |
| Other n-3 | 17.573 | 6.413 | 22.872 | 6.293 | 17.001 | 3.636 |
| Other LC n-3 | 8.946 | 4.508 | 12.751 | 4.501 | 10.25 | 2.7 |
| (FPA + DHA)/ Other LC n-3 | 1.7 | 20 | 3.8 | 20 | 6.6 | 34 |

** GC area of 0.02% or below.
‡Only peaks with area above 0.05% included.

As Table 4A shows, all three concentrates comprised more than 94% n-3 fatty acids, but the relative concentrations of different n-3 and n-6 fatty acids varied significantly. Hexane was the most efficient solvent in relative removal of n-6 fatty acids, as well as removal of n-3 fatty acids other than DHA without substantial loss of EPA or DHA in the final product (loss of about 15%). The high ratio of DPA(n-3):DHA=3.3:1 suggests that the hexane extract may be suitable for purification of DPA(n-3). Similarly, the low value of 1.7 for the ratio (EPA+DHA):(other LC n-3) indicates that the hexane extract may be suitable for production of concentrates with high relative contents of other LC omega-3 fatty acids. The hexene extract contained a higher total concentration of n-3 fatty acids than the hexane extract, with a ratio DPA(n-3):DHA of approximately 1:1. The hexene extract may also be a suitable raw material for producing such concentrates and individual pure fatty acid esters. Cyclohexene gave a concentrate lower in n-6 fatty acids than the other solvents (n-6 fatty acids were substantially absent), and low in n-3 fatty acids other than EPA and DHA, but also provided lower yield of EPA and DHA in the final product (loss of about 68%). The sum of EPA+DHA in the concentrate was about 91.0%, while the sum of other $C_{20}$-$C_{22}$ n-3 fatty acids ("other LC n-3") was only 2.7%.

Results in Tables 3 and 4A indicate that varying the temperature and using different relative amounts of starting fatty acid mixture and solvent affects the composition of the concentrate obtained. For example, the results shown in Table 3 were obtained using the same volumes of K30EE and 1-hexene as those in Table 4A, but with only 2/3 the volume of 70% wt. $AgNO_3$ solution. The temperatures used were also different (room temperature vs. 70° C.).

Studies were also performed with 1,7-octadiene; however, this solvent resulted in a very exothermic reaction. The exothermic reaction indicates a high affinity of cyclooctadienes and other dienes/polyenes to silver ions, which could make these compounds useful as displacement liquids, provided that adequate safety measures were applied. See also Example 2B at Table 4B.

Example 2B

Additional Example on the Use of Displacement Liquids

A number of experiments were performed with the organic solvents listed in Table 4B. For each experiment the following approximate amounts of reagents and ethyl ester starting materials were used: 60 g silver nitrate, dissolved in water to give 70% concentration (25.7 g water), and 48 g K30EE ethyl ester (batch 2101071). The exact amounts, as well as amounts of extracts recovered, are given in Table 4C.

After stirring with a magnetic stirrer at room temperature for 1.5 hours, each mixture of aqueous silver nitrate solution and K30EE was transferred to a separatory funnel, and allowed to sit in darkness until phase separation occurred. The upper organic layer ("non-dissolved esters") was removed. A sample for analysis was collected for the first experiment in the series.

With the exception of the first experiment in the series, the aqueous phase was extracted with three portions of solvent. Each portion contained approx. 0.36 mol of solvent. It is estimated that around 20 g of ethyl esters remained in the aqueous phase after removal of non-dissolved esters. Assuming that the average molecular weight of the ethyl esters is 330 g/mol, 20 g ethyl esters corresponds to 0.06 mol. This means that each extraction was carried out with an estimated 6 times molar excess of solvent compared to the ethyl esters originally dissolved in the aqueous phase. See Table 4B.

After extraction was completed, 600 ml of water was added to the aqueous phase, and after vigorous stirring, the mixture was left in darkness overnight for a new phase separation to be completed.

All extracts involving solvents were evaporated under vacuum using a rotating evaporator. After weighing the extracts, samples were taken for analysis.

Analytical results from selected fatty acid ethyl esters are given in Table 4C.

TABLE 4B

Amounts of solvents

| Extraction solvent | Density (g/ml) | Molecular weight (g/mol) | Approx. weight of solvent for each of three extractions (g) | Approx. volume of solvent for each of three extractions (ml) | Number of moles for each extraction and for total |
|---|---|---|---|---|---|
| 1. No solvent | — | — | — | — | — |
| 2. Hexane | 0.66 | 86.2 | 31.3 | 47.3 | 0.36 (1.09) |
| 3. 1-Hexene | 0.673 | 84.2 | 30.6 | 45.5 | |
| 4. Cyclohexene | 0.811 | 82.1 | 29.8 | 36.7 | |
| 5. Dichloromethane | 1.335 | 84.9 | 30.8 | 23.1 | |
| 6. 1,5-Cyclooctadiene | 0.882 | 108.2 | 39.3 | [1] | |
| 7. Acetone | 0.788 | 58.1 | 21.1 | [2] | |

[1] Addtion of 1,5-cyclooctadiene to the aqueous silver nitrate-containing phase resulted in an exothermic reaction, and for safety reasons the experiment was abandoned. However, this exothermic reaction indicates a high affinity of cyclooctadienes and other dienes/polyenes to silver ions, which could make these compounds useful as displacement liquids, provided that adequate safety measures were applied.

[2] Addition of acetone did not result in phase separation. Further experiments could be performed, for example, combining acetone with other solvents or using other ketones than acetone.

TABLE 4C

Weights of reagents, starting material and extracts (g)[1]

| Solvent | AgNO$_2$ | H$_2$O | K30EE | Undissolved ester | Extracts A | B | C | Concentrate | Sum of recovered material | Total yield (%) |
|---|---|---|---|---|---|---|---|---|---|---|
| None | 60.6 | 26.0 | 48.7 | 28.2 | | | | 18.5 | 46.7 | 96 |
| Hexane | 60.1 | 25.4 | 48.1 | 29.2 | 1.17 | 0.96 | 0.72 | 13.8 | 45.9 | 95 |
| 1-Hexene | 60.5 | 25.3 | 48.1 | 32.0 | 1.41 | 0.87 | 0.68 | 11.3 | 45.9 | 96 |
| Cyclohexene | 60.2 | 25.1 | 49.1 | 29.0 | 4.55 | 3.50 | 1.59 | 9.48 | 48.1 | 98 |
| CH$_2$Cl$_2$ | 60.1 | 25.3 | 48.1 | 26.3 | 8.40 | 3.00 | 1.92 | 6.16 | 45.8 | 95 |

[1] It is difficult to obtain exact weights after separation of small volumes. Some material will inevitably be lost on the surface of the glass equipment, and it is difficult to avoid some contamination from the aqueous phase. The skilled person will realize that there is some uncertainty with regards to the weight of the various extracts, as well as the total yield.

TABLE 4D

GC results (normalized area percent) for selected fatty acid ethyl esters.

| Solvent (fraction) | Fraction | 16:4n-1 | 18:3n-3 | 18:4n-3 | 19:5 | 20:4n-6 | 20:4n-3 | EPA | 21:5n-3 | 22:5n-6 | 22:5n-3 | DHA |
|---|---|---|---|---|---|---|---|---|---|---|---|---|
| — | K30EE | 2.0 | 0.6 | 2.4 | nd | 1.0 | 0.8 | 18.7 | 0.7 | 0.4* | 2.2 | 12.6 |
| None | Undissolved ester | 0.2 | 0.7 | 1.0 | 0.3 | 1.0 | 0.6 | 1.7 | 0.1 | 0.3 | 0.5 | 0.6 |
| | Concentrate | 3.6 | 0.2 | 4.2 | 0.2 | 0.7 | 0.7 | 39.4 | 1.5 | 0.6 | 4.3 | 27.2 |
| | CF | 1.8 | 0.3 | 1.8 | — | 0.7 | 0.9 | 2.1 | 2.1 | 1.5 | 2.0 | 2.2 |
| Hexane | A | 7.5 | 0.4 | 13.8 | 0.2 | 4.8 | 4.9 | 30.3 | 1.8 | 2.8 | 10.0 | 3.7 |
| | B | 4.5 | 0.4 | 14.5 | 0.1 | 2.1 | 2.8 | 39.0 | 2.4 | 2.2 | 11.4 | 4.7 |
| | C | 4.9 | 0.3 | 13.4 | 0.0 | 1.4 | 1.9 | 42.8 | 2.5 | 1.7 | 11.3 | 5.2 |
| | Concentrate | 4.6 | 0.0 | 2.3 | 0.2 | 0.1 | 0.1 | 42.7 | 1.4 | 0.2 | 2.9 | 34.1 |
| | CF | 2.3 | 0 | 1.0 | — | 0.1 | .1 | 2.3 | 2.0 | 0.5 | 1.3 | 2.7 |
| 1-Hexene | A | 4.5 | 0.3 | 12.0 | 0.1 | 2.6 | 2.9 | 39.1 | 2.1 | 1.8 | 8.6 | 6.5 |
| | B | 2.5 | 0.3 | 12.1 | 0.2 | 1.6 | 2.1 | 46.4 | 2.4 | 1.6 | 9.2 | 7.9 |
| | C | 5.3 | 0.2 | 11.0 | 0.2 | 0.7 | 1.3 | 49.6 | 2.5 | 1.2 | 8.9 | 8.5 |
| | Concentrate | 5.2 | 0.0 | 2.2 | 0.2 | 0.0 | 0.0 | 46.5 | 1.5 | 0.2 | 3.0 | 40.4 |
| | CF | 2.6 | 0 | 0.9 | — | 0 | 0 | 2.5 | 2.1 | 0.5 | 1.4 | 3.2 |
| Cyclohexene | A | 2.3 | 0.3 | 6.5 | 0.2 | 1.8 | 1.8 | 27.6 | 1.4 | 1.2 | 5.7 | 6.5 |
| | B | 3.3 | 0.3 | 6.8 | 0.1 | 1.0 | 1.2 | 37.3 | 1.8 | 0.9 | 6.2 | 9.7 |
| | C | 4.9 | 0.1 | 7.3 | 0.2 | 0.5 | 0.8 | 52.1 | 2.3 | 0.8 | 7.1 | 14.5 |
| | Concentrate | 5.5 | 0.0 | 1.9 | 0.2 | 0.0 | 0.1 | 43.9 | 1.4 | 0.1 | 2.3 | 43.9 |
| | CF | 3.3 | 0 | 0.8 | — | 0 | 0.1 | 2.3 | 2.0 | 0.3 | 1.0 | 3.5 |
| Dichloromethane | A | 2.5 | 0.2 | 6.0 | 0.2 | 1.5 | 1.4 | 22.2 | 1.2 | 1.0 | 4.7 | 3.7 |
| | B | 6.7 | 0.2 | 7.8 | 0.2 | 0.5 | 0.9 | 55.9 | 2.7 | 0.9 | 8.4 | 10.2 |
| | C | 7.8 | 0.0 | 4.3 | 0.2 | 0.1 | 0.2 | 63.4 | 2.7 | 0.4 | 6.0 | 13.0 |

TABLE 4D-continued

GC results (normalized area percent) for selected fatty acid ethyl esters.

| Solvent (fraction) | Fraction | 16:4n-1 | 18:3n-3 | 18:4n-3 | 19:5 | 20:4n-6 | 20:4n-3 | EPA | 21:5n-3 | 22:5n-6 | 22:5n-3 | DHA |
|---|---|---|---|---|---|---|---|---|---|---|---|---|
| | Concentrate | 3.5 | 0.0 | 0.4 | 0.2 | 0.0 | 0.0 | 39.1 | 0.9 | 0.0 | 0.9 | 54.8 |
| | CF | 1.8 | 0 | 0.2 | — | 0 | 0 | 2.1 | 1.3 | 0 | 0.4 | 4.3 |

CF = "Concentration factor," i.e. relative GC area in concentrate divided by relative GC area in K30EE
*Estimate based on peak size
nd: not detected

TABLE 4E

Experiment with dichloromethane as displacement liquid.

| Fraction (mass, g) | Volume $CH_2Cl_2$ (ml) | 16:4n-1 | 18:3n-3 | 18:4n-3 | 19:5 | 20:4n-6 | 20:4n-3 | EPA | 21:5n-3 | 22:5n-6 | 22:5n-3 | DHA |
|---|---|---|---|---|---|---|---|---|---|---|---|---|
| K30EE | — | 20 | 0.6 | 2.4 | nd | 1.0 | 0.8 | 18.7 | 0.7 | 0.4* | 2.2 | 12.6 |
| A (6.75) | 8.0 | 1.0 | 0.8 | 3.5 | nd | 1.6 | 1.2 | 8.0 | 0.3 | 0.6 | 2.2 | 1.2 |
| B (1.88) | 8.0 | 4.3 | 0.5 | 10.9 | nd | 2.0 | 2.2 | 37.0 | 1.9 | 1.5 | 7.5 | 6.2 |
| C (1.72) | 8.0 | 6.1 | 0.2 | 11.5 | 0.2 | 1.1 | 1.6 | 50.8 | 2.6 | 1.4 | 9.4 | 8.6 |
| D (2.73) | 23.1 | 7.6 | 0.1 | 7.6 | 0.2 | 0.2 | 0.5 | 59.0 | 2.8 | 0.7 | 8.3 | 10.4 |
| E (1.77) | 23.1 | 8.4 | 0.0 | 4.0 | 0.2 | 0.1 | 0.2 | 63.4 | 2.6 | 0.3 | 5.8 | 12.7 |
| Concentrate (6.34) | | 3.7 | 0.0 | 0.4 | 0.2 | 0.1 | 0.0 | 39.0 | 0.9 | 0.1 | 0.9 | 53.8 |
| CF | | 1.9 | 0 | 1.7 | — | 0.1 | 0 | 2.1 | 1.3 | 0.3 | 0.4 | 4.3 |

GC results (normalized area percent) for selected fatty acid ethyl esters.
CF = "Concentration factor," i.e. relative GC area in concentrate divided by relative GC area in K30EE.
*Estimate based on peak size
nd: not detected As can be seen from Table 4D, the various solvents worked as displacement liquids in different ways. The following discussion focuses on only a few of the many different possibilities that exist for making use of these solvents for production of raw material for concentrates of various fatty acid ethyl esters (or combinations of ethyl esters). The person skilled in the art will realize that the results showed possibilities for making raw materials for a number of further fatty acid ethyl esters or combinations of fatty acid ethyl esters.

While hexane was found to have the useful property of enabling the production of fractions rich in DPA (22:5n-3) compared to DHA, and thus deemed useful for production of concentrates of DHA (and from the tabulated values also for production of concentrates enriched in 20:4n-3), dichloromethane ($CH_2Cl_2$) may be, for example, well adapted for the production of concentrates of EPA and DHA that contain low amounts of other n-3 fatty acids as well as low values of n-6 fatty acids. In addition, compared to the other displacement liquids, $CH_2Cl_2$ also had the effect of reducing the relative amount of the highly unsaturated fatty acid 16:4n-1. Thus, $CH_2Cl_2$, or displacement liquids with similar effects, may be useful for production of high concentrates of EPA and DHA, because they may eliminate the need for reduction of the 16:4n-1 with supplementary separation techniques that work according to chain length. Molecular distillation/short path distillation is a commonly used separation technique according to chain length. However, as the separation power of this technique may be modest, removal of fatty acids 16:4n-1 by molecular distillation/short path distillation may also result in some loss of the desired fatty acids. Thus, the value is using a displacement liquid like $CH_2Cl_2$ to reduce the content of 16:4n-1 compared to other displacement liquids.

Table 4C shows that when dichloromethane was used as a displacement liquid, a relatively large amount of ethyl ester was taken out in the first fraction (fraction A). Table 4E shows the results from a further experiment with dichloromethane as displacement agent. The procedure was identical to that given in Tables 4B and 4C, except that the first extraction with 23.1 ml $CH_2Cl_2$ was substituted with three extractions, each with 8 ml $CH_2Cl_2$.

The final amount of concentrate (6.34 g) was close to that obtained in the first example with $CH_2Cl_2$. The concentrations of EPA and DHA as well as the concentrations of other fatty acids were also very close to those obtained in the first example (see Table 4D). The composition of extract A exhibited low amounts of EPA and DHA, and high relative amounts of other long-chain omega-3 fatty acids and also of long-chain omega-6 fatty acids. Thus, for example it was found that small volumes of dichloromethane could be utilized to improve the content of EPA and DHA, and reduce the content of other long-chain n-3 fatty acids and of long-chain n-6 fatty acids. By varying the amount(s) of $CH_2Cl_2$, different compositions will be obtained, either as extract or as concentrates. From the information in this example, by utilizing specific ratios of $CH_2Cl_2$ compared to the amount and concentration of starting material, one may tailor compositions with specific fatty acid contents. As can be seen from Table 4E and Table 4D, further extraction with $CH_2Cl_2$ to a large extent removed the other long-chain n-3 fatty acids and the long-chain n-6 fatty acids, giving a concentrate after water dilution that contained more than 90% of the ethyl esters of EPA plus DHA (GC area %). The intermediate extracts therefore represented useful starting materials for production of enriched fractions of such long-chain n-3 and n-6 fatty acids. Also, the intermediate products were enriched in EPA, making them useful as intermediates for production of products containing high concentrations of EPA, like for example the product Epadel.

Figure 5:
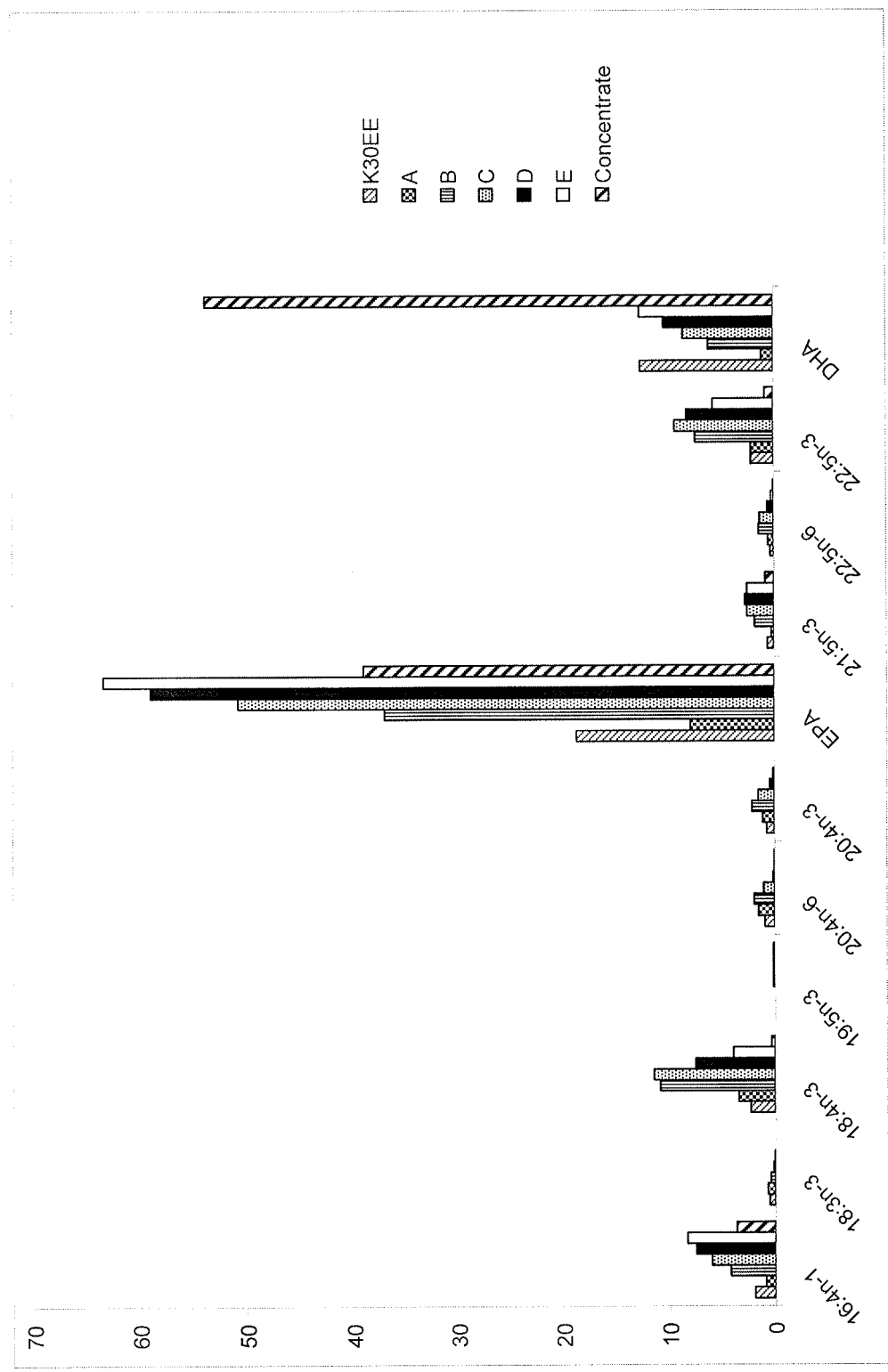
FIG. 5 is a chart representing the relative concentration of ethyl esters of specific selected fatty esters, as described in Example 2B at Table 4E.

FIG. 5 represents the same data as Table 4E, with columns representing the relative concentration of ethyl esters of the same selected fatty esters. From the Figure and from the Tables, a "pecking order" for the ease of removal of fatty acid ethyl esters with $CH_2Cl_2$ as displacement liquid can be inferred, based on when the maximum extraction of a specific component is obtained, and compared to the ratio of the relative concentration in K30EE and Extract A, as well as the ratio between the relative concentration in Extract E and the final concentrate.

This "pecking order" seems to be:
18:3n-3>20:4   n-6>22:5n-6>20:4n-3>18:4n-3>22:5n-3>21:5n-3>16:4n-1>EPA>DHA The 19:5 fatty acid is present in such low amounts that it has not been possible to find its place in this "pecking order."

Analysis by high performance size exclusion chromatography (HPSEC) showed that partial glycerides, which are typical minor constituents in ethylated oils, were enriched in the concentrates when using $CH_2Cl_2$ as a displacement liquid. For the other solvents used, the concentration of partial glycerides in the concentrates did not appear to be affected to a significant degree compared to the starting K30EE. This is illustrated with analytical results given in Table 4F:

TABLE 4F

Partial glycerides. Ananlyzed according the procedure in Ph.Eur. Monograph 1250 and USP Monograph for Omega-3 acid ethyl esters

| Solvent | Fraction | Diglycerides | Monoglycerides | Ethyl esters |
|---|---|---|---|---|
| | K30EE | 2.9 | 4.0 | 93.1 |
| None | Concentrate | 2.5 | 3.0 | 94.5 |
| Hexane | Concentrate | 2.2 | 2.7 | 95.1 |
| 1-Hexane | Concentrate | 2.4 | 3.4 | 94.2 |
| Cyclohexene | Concentrate | 2.6 | 3.7 | 93.7 |
| $CH_2Cl_2^1$ | Concentrate | 3.5 | 6.0 | 90.5 |
| $CH_2Cl_2^2$ | A | 4.0 | 1.8 | 94.2 |
| | B | 2.1 | 0.9 | 97.0 |
| | C | 1.9 | 0.8 | 97.3 |
| | D | 1.9 | 0.8 | 97.3 |
| | E | 1.3 | 0.9 | 97.8 |
| | Concentrate | 3.4 | 7.2 | 89.4 |

[1]Concentrate from Table 4D
[2]Extract and concentrates from Table 4E

The GC area results in Tables 4D and 4E were obtained by direct injection of the ethyl ester samples as described by the European Pharmacopeia Monograph 2.4.29 and the USP Monograph Omega-3 acid ethyl esters. If the partial glycerides in the samples resemble the composition of the starting K30EE, the skilled person will realize that inclusion of the partial glycerides in the analysis leads to a reduction of the measured content of EPA and DHA. The reason for this is that the partial glycerides will not be observed in the GC chromatogram, and for this reason the relative area percent of the ethyl ester peaks will be higher than if all components were observed in the chromatogram. The skilled person will realize that a method for including the partial glycerides in the analysis would be to methylate the samples, thereby transforming both the ethyl esters and the partial glycerides to methyl esters. Thus, it would appear likely that when performing such a procedure for the concentrates obtained by using $CH_2Cl_2$ as a displacement liquid, the content of EPA and DHA would be reduced compared to the results given in Tables 4D and 4E.

However, when the concentrates obtained using $CH_2Cl_2$ as a displacement liquid were methylated, the resulting methyl esters did not have a reduced content of EPA and DHA. On the contrary, while the concentration of EPA seemed to be more or less unaffected, the concentration of DHA seemed to have increased (Table 4G). At the same time, the relative concentration of 16:4n-1 seemed not to have increased, but rather to have been slightly reduced. Thus it appears that when using a displacement liquid like $CH_2Cl_2$, the concentration of partial glycerides was, for example, increased in the final concentrate, and those partial glycerides had a strongly increased concentration of, for example, EPA and DHA compared to the starting K30EE. Thus, valuable fatty acids that are lost with the partial glycerides fractions in traditional concentration procedures like molecular distillation and urea fractionation are retained and concentrated according to the process disclosed herein.

TABLE 4G

Concentrates obtained using $CH_2Cl_2$ as displacement liquid. Methylation was performed according to procedure as for derivatization of triglycerides, European Pharmacopoeia Monograph 2.4.29, and for derivatization when analyzing partial glycerides in USP Monograph Omega-3 acid ethyl esters.

| | | 16:4n-1 | DHA | EPA |
|---|---|---|---|---|
| From Table 4D | Analyzed as ethyl ester | 3.5 | 39.1 | 64.8 |
| | Analyzed after methylation | 3.4 | 38.9 | 55.2 |
| From Table 4E | Analyzed as ethyl ester | 3.7 | 39.0 | 53.8 |
| | Analyzed after methylation | 3.4 | 39.2 | 54.9 |

From this example, $CH_2Cl_2$ had for example improved effects as a displacement liquid compared to hydrocarbons that contain only carbon and hydrogen. The skilled person will realize that similar improved effects may be obtained by other halogenated solvents, as well as solvents containing other polar functional groups, like oxygen or nitrogen.

Example 2C.

Enrichment of EPA and DHA Using Triglycerides as Starting Material 60.3 g of cod liver oil (Møller's Tran) was added to a mixture of 23 g $H_2O$ and 59 g $AgNO_3$ at 70° C. The mixture was stirred for one hour and then allowed to stand until phase separation occurred. The lower aqueous phase was separated from the upper oil phase and 400 g of water was added in order to dissociate the $Ag^+$ complex and releasing triglycerides enriched in EPA and DHA. The fatty acid profiles of the starting material and the resulting oil are given in Table 4H. EPA and DHA showed more than a two-fold increase. The example shows that complexation also occurs with triglycerides. In order to achieve an enrichment of EPA and DHA, the distribution of the fatty acids cannot be totally random among the triglycerides. Some of the triglycerides must have predominantly saturated or unsaturated fatty acids connected to the backbone. The distribution of the fatty acids in the triglyceride can vary depending on the species.

TABLE 4H

Example of enrichment of EPA and DHA using cod liver oil as starting material

| Fatty acid | Cod liver oil (TG) | Concentrate | Change |
|---|---|---|---|
| C14:0 | 3.0 | 1.4 | −53% |
| C16:0 | 9.7 | 5.0 | −49% |
| C16:1 | 8.2 | 3.8 | −54% |
| C18:0 | 2.1 | 1.5 | −29% |
| C18:1n-9 | 17.8 | 9.6 | −46% |
| C18:1n-7 | 4.9 | 3.1 | −37% |
| C18:2 | 1.8 | 1.0 | −45% |
| C18:3n-3 | 0.8 | 0.6 | −18% |
| C8:4n-3 | 2.5 | 3.7 | 51% |

TABLE 4H-continued

Example of enrichment of EPA and DHA using cod liver oil as starting material

| Fatty acid | Cod liver oil (TG) | Concentrate | Change |
|---|---|---|---|
| C20:1 | 13.3 | 6.5 | −51% |
| C20:4n-3 | 0.8 | 0.9 | 11% |
| C20:5n-3 | 9.4 | 19.8 | 110% |
| C22:1 | 7.2 | 2.9 | −60% |
| C22:5n-3 | 1.3 | 2.0 | 51% |
| C22:6n-3 | 13.0 | 33.7 | 160% |

Example 2D

Extraction with Supercritical $CO_2$

Using a $AgNO_3/H_2O/EE$ ratio of 45%/19%/36% (on a weight basis) at 50° C., 68% of the ethyl esters remained in the organic layer. The aqueous layer was transferred to the SFE (Supercritical Fluid Extraction) column for extraction. Not all of the ethyl esters from the complex could be extracted, contrary to what was found by Suzuki (Suzuki et al. (1993), Bioseparation 3, pp 197-204). After about 70% of the ethyl esters had been extracted, the remaining mixture had turned into a gel-like solid. The temperature and pressure of extraction can be utilized to vary the EPA/DHA ratio. Increasing the extraction temperature from 60 to 70° C. at 280 bar changed the EPA/DHA from 53/15 to 55/23 in the extracted ethyl esters. In order to extract all the ethyl esters, it was necessary to add water during the extraction. Adding 0.5% $H_2O$ to the $CO_2$ flow was sufficient to allow complete extraction of the ethyl esters. The results of Example 6 below suggest that addition of ethanol may also be useful in this respect.

Example 3

Dilution in Water

It has been found that a partial dilution of the aqueous phase with water will release an organic fraction enriched in n-6 fatty acids and/or specific omega-3 fatty acids (e.g., long-chain n-3 fatty acids other than EPA and DHA).

Figure 4:
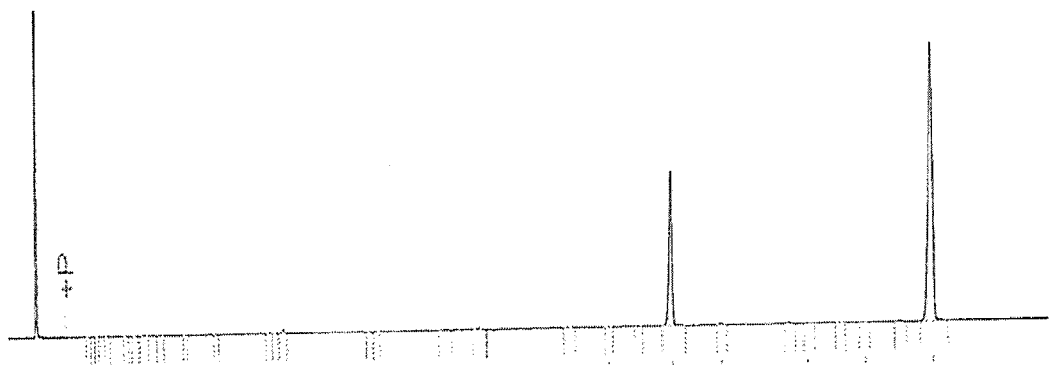
FIG. 4 is a gas chromatogram of Concentrate 4, as described in Example 3 at Table 5.

K85EE was stirred with 60% wt. $AgNO_3$ solution (K85EE:$AgNO_3$=about 7:10 by weight). The aqueous phase was separated from the organic phase and gradually diluted with water. "Concentrate-1" was obtained after one dilution of water (water:$AgNO_3$(s)=about 1.2:1 by weight). A second fatty acid concentrate was obtained by further dilution of the aqueous phase (water:$AgNO_3$(s)=about 2.8:1 by weight) (not analyzed). "Concentrate-4" was obtained by further dilution (water:$AgNO_3$(s)=about 20:1 by weight). Table 5 compares the composition (GC area %) of the K85EE starting mixture, the separated organic phase ("undissolved esters"), Concentrate-1, and Concentrate-4. Yields compared to the weight of K85EE starting mixture are given in parentheses. The gas chromatogram for Concentrate-4 appears in FIG. 4.

TABLE 5

Composition of fatty acid concentrates; gradual water dilution.

| Fatty acid ethyl ester | K85EE | Undissolved esters (45%) | Concentrate-1 (22%) | Concentrate-4 (4%) |
|---|---|---|---|---|
| Phytanic acid | 0.11 | 0.29 | 0.02 | ** |
| 16:3n-4 | 0.11 | 0.22 | 0.07 | ** |
| 16:4n-1 | 0.19 | 0.14 | 0.15 | 0.45 |
| 18:2n-6 | 0.04 | 0.10 | ** | ** |
| 18:3n-4 | 0.11 | 0.26 | 0.03 | ** |
| 18:3n-3 | 0.06 | 0.13 | 0.03 | ** |
| 18:4n-3 | 1.68 | 2.62 | 1.66 | 0.18 |
| 18:4n-1 | 0.11 | 0.17 | 0.15 | ** |
| Furan acid 5 | 0.15 | 0.37 | ** | ** |
| 19:5 | 0.07 | 0.07 | 0.07 | 0.13 |
| 20:3n-6 | 0.06 | 0.14 | ** | ** |
| 20:4n-6 | 1.71 | 3.86 | 0.61 | ** |
| Furan acid 7 | 0.15 | 0.29 | 0.04 | 0.06 |
| 20:4n-3 | 0.45 | 0.95 | 0.24 | ** |
| Furan acid 8 | 0.45 | 1.11 | 0.05 | ** |
| 20:5n-3 (EPA) | 48.65 | 52.76 | 54.39 | 27.39 |
| Furan acid 9 | 0.07 | 0.16 | ** | ** |
| 21:5n-3 | 1.74 | 2.38 | 2.14 | 0.25 |
| 22:4 | 0.08 | 0.17 | ** | ** |
| Furan acid 10 | 0.28 | 0.68 | ** | ** |
| 22:5n-6 | 0.90 | 1.87 | 0.53 | ** |
| Furan acid 11 | 0.04 | 0.12 | ** | ** |
| 22:5n-3 | 2.87 | 5.08 | 3.08 | 0.19 |
| 22:6n-3 (DHA) | 39.55 | 25.15 | 36.16 | 70.14 |
| 24:1 | 0.02 | ** | ** | ** |
| EPA + DHA | 88.20 | 77.91 | 90.53 | 97.54 |
| Σn-3 | 95.00 | 89.02 | 97.69 | 98.15 |
| Σn-6 | 2.65 | 5.83 | 1.14 | ** |
| Σn-3/n-6 | 35.8 | 15.3 | 85.7 | ∞‡ |
| Σ"Other C20-C22 n-3" | 5.06 | 8.41 | 5.46 | 0.44 |

**GC area of 0.02% or below.
‡Only peaks above 0.05% included

The results in Table 5 show that the organic phase was enriched in n-6 fatty esters compared to the K85EE starting mixture. Similar results were observed for n-3 fatty acids other than DHA. Concentrate 4 contains 70% DHA (GC area %) and very little DPA making such and similar fractions suitable as intermediates for production of pure DHA.

Example 4

$AgNO_3$ Concentration

K85EE was stirred with either 60% wt. or 70% wt. $AgNO_3$ solution with K85EE:$AgNO_3$=2:1 (20.0 g to 10.1 g). The oil/water mixture was allowed to separate and the organic phase was removed. The aqueous phase was diluted with 100 ml water, and the fatty acid concentrate ("Concentrate-1") released by the dilution was collected. An additional 50 ml water was added to the aqueous phase to obtain a second concentrate ("Concentrate 2"). The composition of the K85EE starting mixture, the separated organic phase ("undissolved esters"), and Concentrates 1 and 2 were determined by GC analysis (GC area %) as shown in Tables 6 and 7. Yields compared to the weight of K85EE starting mixture are given in parentheses.

TABLE 6

Composition of fatty acid concentrates; 60% AgNO₃ solution.

| | | Concentration (GC area %) | | |
|---|---|---|---|---|
| Fatty acid ethyl ester | K85EE | Undissolved esters (22%) | Concentrate-1 (64%) | Concentrate-2 (8%) |
| 18:2n-6 | 0.04 | 0.05 | ** | ** |
| 18:3n-4 | 0.11 | 0.21 | ** | ** |
| 18:3n-3 | 0.06 | 0.08 | ** | ** |
| 18:4n-3 | 1.68 | 3.01 | 1.10 | 0.58 |
| 20:4n-6 | 1.71 | 6.75 | 0.46 | 0.10 |
| 20:4n-3 | 0.45 | 1.67 | 0.18 | 0.03 |
| Furan acid 8 | 0.45 | 1.62 | 0.03 | ** |
| 20:5n-3 EPA | 48.65 | 47.84 | 46.03 | 39.95 |
| 21:5n-3 | 1.74 | 2.57 | 1.77 | 0.81 |
| 22:5n-6 | 0.90 | 3.22 | 0.46 | 0.07 |
| 22:5n-3 | 2.87 | 6.56 | 2.81 | 0.54 |
| 22:6n-3 DHA | 39.55 | 19.54 | 46.02 | 57.12 |
| 24:1 | 0.02 | 0.04 | ** | ** |
| Σn-3 | 95.00 | 81.27 | 97.91 | 93.03 |
| Σn-6 | 2.65 | 10.02 | 0.92 | 0.17 |
| Σn-3/n-6 | 35.8 | 8.11 | 106 | 547 |
| Σ"other C20-C22 n-3" | 5.06 | 10.80 | 4.76 | 1.38 |

**GC area of 0.02% or below

TABLE 7

Composition of fatty acid concentrates; 70% AgNO₃ solution.

| | | Concentration (GC area %) | | |
|---|---|---|---|---|
| Fatty acid ethyl ester | K85EE | Undissolved (15%) | Concentrate 1 (71%) | Concentrate 2 (9%) |
| 18:2n-6 | 0.04 | 0.13 | ** | ** |
| 18:3n-4 | 0.11 | 0.24 | ** | ** |
| 18:3n-3 | 0.06 | 0.15 | ** | ** |
| 18:4n-3 | 1.68 | 2.70 | 1.31 | 0.62 |
| 20:4n-6 | 1.71 | 9.65 | 0.80 | 0.10 |
| 20:4n-3 | 0.45 | 1.96 | 0.29 | 0.03 |
| Furan acid 8 | 0.45 | 1.16 | ** | ** |
| 20:5n-3 (EPA) | 48.65 | 46.43 | 48.21 | 40.84 |
| 21:5n-3 | 1.74 | 2.38 | 1.94 | 0.85 |
| 22:5n-6 | 0.90 | 3.90 | 0.71 | 0.07 |
| 22:5n-3 | 2.87 | 6.43 | 3.10 | 0.53 |
| 22:6n-3 (DHA) | 39.55 | 17.72 | 42.66 | 56.37 |
| 24:1 | 0.02 | 0.09 | ** | ** |
| Σn-3 | 95.00 | 77.77 | 97.51 | 99.24 |
| Σn-6 | 2.65 | 13.68 | 1.54 | 0.17 |
| Σn-3/n-6 | 35.8 | 5.69 | 63.3 | 584 |
| Σ"other C20-C22 n-3" | 5.06 | 10.77 | 5.33 | 1.41 |

**GC area of 0.02% or below

It may also be possible to obtain a fatty acid concentrate with an aqueous solution comprising a relatively low concentration of silver ions. However, dilution by water may be preferable in order to obtain two types of mixtures: a fatty acid concentrate comprising higher amounts of EPA and DHA (i.e., lower amounts of omega-6 fatty acids and/or specific omega-3 fatty acids such as long-chain omega-3 fatty acids other than EPA and DHA), and another concentrate (e.g., separated organic phase) comprising higher amounts of omega-6 fatty acids and/or specific omega-3 fatty acids such as long-chain omega-3 fatty acids other than EPA and DHA (i.e., lower amounts of EPA and DHA). This is illustrated in Table 8 as follows. K30EE was mixed with AgNO₃ solution (60% wt., 70% wt., or 80% wt.) with K30EE:AgNO₃=0.8, and the two resulting phases were separated. The aqueous phase was diluted in water. For each AgNO₃ concentration in Table 8, the column marked (1) gives the composition of the separated organic phase, while column (2) gives the composition of the fatty acid concentrate recovered by diluting the aqueous phase in water at a temperature of about 70° C. As shown in Table 8, the 60% AgNO₃ solution gave higher n-3/n-6 ratios and a higher DHA concentration.

TABLE 8

Composition of fatty acid concentrates; 60%, 70%, 80% AgNO₃ solutions.

| | | 80% AgNO₃ | | 70% AgNO₃ | | 60% AgNO₃ | |
|---|---|---|---|---|---|---|---|
| Fatty acid ethyl ester | K30EE | 1 (69.1%) | 2 (27.2%) | 1 (73.2%) | 2 (25.0%) | 1 (80.3%) | 2 (17.3%) |
| 16:4n-1 | 2.04 | 0.42 | 5.42 | 0.63 | 5.54 | 1.00 | 6.23 |
| 18:2n-6 | 1.20 | 0.02 | 0.02 | 0.02 | 0.02 | 0.02 | ** |
| 18:3n-3 | 0.60 | 0.71 | 0.09 | 0.69 | 0.07 | 0.64 | 0.04 |
| 18:4n-3 | 2.15 | 1.22 | 3.60 | 1.64 | 2.94 | 2.04 | 2.08 |
| 20:4n-6 | 1.05 | 1.09 | 0.53 | 1.16 | 0.27 | 1.13 | 0.10 |
| 20:4n-3 | 0.80 | 0.55 | 0.56 | 0.66 | 0.32 | 0.68 | 0.13 |
| Furan acid 8 | — | 0.13 | 0.02 | 0.14 | ** | 0.13 | ** |
| 20:5n-3 (EPA) | 18.53 | 3.11 | 43.15 | 5.83 | 42.79 | 10.33 | 41.29 |
| 21:5n-3 | 0.73 | 0.20 | 1.59 | 0.31 | 1.46 | 0.52 | 1.18 |
| 22:5n-6 | 0.5 | 0.31 | 0.59 | 0.44 | 0.36 | 0.48 | 0.14 |
| 22:5n-3 | 2.33 | 0.91 | 4.37 | 1.55 | 3.45 | 2.16 | 2.05 |
| 22:6n-3 (DHA) | 12.87 | 0.65 | 31.53 | 1.32 | 34.14 | 3.21 | 39.88 |
| EPA + DHA | 30.87 | 3.76 | 74.60 | 7.15 | 76.93 | 13.54 | 81.17 |
| Σn-3 | 37.43 | 7.35 | 84.81 | 12.35 | 85.17 | 19.58 | 86.65 |
| Σn-6 | 1.55 | 1.42 | 1.14 | 1.62 | 0.65 | 1.63 | 0.24 |
| Σn-3/Σn-6 | 24 | 5.18 | 74.4 | 7.62 | 131 | 12.0 | 361 |
| Σ"Other C₂₀-C₂₂ n-3" | 3.86 | 4.77 | 6.52 | 2.52 | 5.23 | 3.36 | 3.36 |

** Area percent of 0.02% or below.

Example 5

Fatty Acid Mixture:AgNO₃ Ratio

The effect of varying the amount of starting fatty acid mixture to AgNO$_3$(s) was studied by varying the ratio K30EE:AgNO$_3$ from 0.4 to 1.6. A 70% wt. aqueous solution of AgNO$_3$ was used in all experiments. After stirring the combined K30EE-AgNO$_3$ for 1.5 hours at 70° C., phase separation was allowed to occur at the same temperature. In each experiment, two visually clear phases were obtained after about one hour. After removing the organic phase, the aqueous solutions were diluted with water (water:AgNO$_3$(s) =about 7.5:1 by weight). The concentrates obtained are shown in Table 9. Compositions were determined by GC analysis (GC area %). The results in Table 9 indicate that increasing the amount of K30EE per AgNO$_3$ gives higher n-3/n-6 ratios, as well as higher ratios of (EPA+DHA)/Σ (other LC n-3).

TABLE 9

Composition of fatty acid concentrates; K30EE:AgNO₃ ratios 0.4-1.6

| Fatty acid ethyl ester | K30EE | K30EE:AgNO₃(s) | | | |
|---|---|---|---|---|---|
| | | 0.4 | 0.8 | 1.2 | 1.8 |
| 16:4n-1 | 2.04 | 5.93 | 6.34 | 6.69 | 6.77 |
| 18:3n-3 | 0.6 | 0.05 | ni | ni | 0.05 |
| 18:4n-3 | 2.15 | 3.28 | 2.33 | 1.99 | 1.88 |
| 20:4n-6 | 1.05 | 0.27 | 0.19 | 0.15 | 0.17 |
| 20:4n-3 | 0.8 | 0.33 | 0.21 | 0.18 | 0.18 |
| 20:5n-3 (EPA) | 18.53 | 46.23 | 42.5 | 39.75 | 37.62 |
| 21:5n-3 | 0.73 | 1.58 | 1.28 | 1.11 | 1.03 |
| 22:5n-6 | 0.5 | 0.36 | 0.22 | 0.18 | 0.17 |
| 22:5n-3 | 2.33 | 3.54 | 2.42 | 1.98 | 1.83 |
| 22:6n-3 (DHA) | 12.29 | 34.66 | 40.8 | 44.79 | 45.21 |
| EPA + DHA | 30.82 | 80.89 | 83.3 | 84.54 | 82.83 |
| Σn-3 | 37.43 | 89.67 | 89.54 | 89.8 | 87.8 |
| Σn-6 | 1.55 | 0.6 | 0.41 | 0.33 | 0.34 |
| Σn-3/n-6 | 24 | 142 | 218 | 272 | 258 |
| Other n-3 | 6.61 | 8.78 | 6.24 | 5.26 | 4.97 |
| Σ(Other LC n-3) | 3.86 | 5.45 | 3.91 | 3.27 | 3.04 |
| (EPA + DHA)/Σ(Other LC n-3) | 7 | 14 | 21 | 25 | 27 | ni: Not integrated; peaks assumed to be below 0.05 area %

Example 6

Addition of Alcohol

K30EE was stirred with 70% wt. AgNO$_3$ solution comprising increasing relative amounts of ethanol as shown in Table 10. After removing the initial organic phase as described above, the remaining aqueous phase was diluted with water (water:AgNO$_3$(s)=about 7.5:1 by weight). Compositions were determined by GC analysis (GC area %) as shown in Table 10.

TABLE 10

Composition of fatty acid concentrates; addition of ethanol to aqeous phase. K30EE is from the same batch as that of Table 9.

| Fatty acid ethyl ester | Ethanol % (compared to AgNO₃(s)) | | | | |
|---|---|---|---|---|---|
| | 0 | 15 | 30 | 45 | 60 |
| 16:3n-4 | 1.066 | 1.937 | 2.68 | 2.89 | 2.908 |
| 16:4n-1 | 3.399 | 3.366 | 3.235 | 3.084 | 2.926 |
| 18:1n-9 | 1.852 | 0.738 | 0.741 | 1.238 | 2.175 |
| 18:2n-6 | 0.078 | 0.058 | 0.12 | 0.027 | 0.029 |
| 18:3n-6 | 0.092 | 0.157 | 0.311 | 0.4 | 0.447 |
| 18:3n-4 | 0.045 | 0.092 | 0.178 | 0.23 | 0.243 |
| 18:3n-3 | 0.117 | 0.146 | 0.125 | 0.122 | 0.111 |
| 18:4n-3 | 4.237 | 4.893 | 4.973 | 4.878 | 4.61 |
| 18:4n-1 | 0.528 | 0.61 | 0.613 | 0.598 | 0.57 |
| Furan acid 5 | 0.032 | — | 0.017 | 0.05 | 0.08 |
| 19:5 | 0.149 | 0.159 | 0.156 | 0.156 | 0.144 |
| 20:3n-6 | 0.038 | 0.052 | 0.123 | 0.195 | 0.242 |
| 20:4n-6 | 0.708 | 1.398 | 2.068 | 2.268 | 2.26 |
| Furan acid 7 | 0.042 | 0.043 | 0.051 | 0.057 | 0.061 |
| 20:4n-3 | 0.738 | 1.249 | 1.534 | 1.57 | 1.521 |
| Furan acid 8 | 0.024 | 0.024 | 0.023 | 0.022 | 0.018 |
| trans-EPA | 0.012 | 0.016 | — | 0.015 | 0.013 |
| 20:5n-3(EPA) | 42.63 | 43.79 | 42.21 | 40.46 | 38.07 |
| Furan acid 9 | 0.022 | 0.086 | 0.031 | 0.035 | 0.034 |
| 21:5n-3 | 1.78 | 1.894 | 1.838 | 1.766 | 1.663 |
| 22:4n-6 | 0.027 | 0.075 | 0.157 | 0.191 | 0.204 |
| Furan acid 10 | 0.032 | — | 0.035 | — | 0.033 |
| 22:5n-6 | 0.732 | 1.103 | 1.129 | 1.13 | 1.069 |
| Furan acid 11 | 0.029 | 0.055 | 0.089 | 0.108 | 0.108 |
| 22:5n-3 | 5.247 | 6.019 | 6.077 | 5.822 | 5.492 |
| trans-DHA | 0.037 | 0.025 | 0.068 | 0.026 | 0.031 |
| 22:6n-3(DHA) | 26.61 | 26.72 | 25.45 | 24.42 | 23.02 |
| EPA + DHA | 69.233 | 70.509 | 67.658 | 64.88 | 61.089 |
| EPA/DHS | 1.60 | 1.65 | 1.66 | 1.66 | 1.65 |
| Σn-3 | 81.352 | 84.71 | 82.205 | 79.038 | 74.486 |
| Σn-6 | 1.675 | 2.843 | 3.908 | 4.211 | 4.251 |
| Σn-3/n-6 | 48 | 29 | 21 | 18 | 17 |

TABLE 10-continued

Composition of fatty acid concentrates; addition of ethanol to aqeous phase. K30EE is from the same batch as that of Table 9.

| Fatty acid ethyl ester | Ethanol % (compared to AgNO$_3$(s)) | | | | |
|---|---|---|---|---|---|
| | 0 | 15 | 30 | 45 | 60 |
| Other n-3 | 12.119 | 14.201 | 14.547 | 14.156 | 13.397 |
| Other LC n-3 | 7.765 | 9.162 | 9.449 | 9.158 | 8.676 |
| (EPA + PHA)/other LC n-3 | 8 | 7 | 7 | 7 | 7 |
| Yield overall (%) | 27 | 27 | 30 | 31 | 33 |

The results in Table 10 indicate that adding ethanol affects various polyunsaturated fatty acids differently. Increasing the relative amount of ethanol may cause greater amounts of monounsaturated fatty acids (e.g., 18:1n-9) to enter the aqueous phase. Adding ethanol also appears to lead to increased concentrations of n-6 fatty adds in comparison to n-3 fatty acids. The content of "other LC n-3 acids" also appears to increase compared to the sum of EPA+DHA. These effects may be useful for producing concentrates with high content of "other LC n-3 acids" and/or high content of n-6 fatty adds.

Example 7

Removal of Pollutants

Several persistent organic pollutants (POPs) were added to K30EE and the resulting ethyl ester concentrated according to the process presently disclosed. The resulting oil (i.e., the fatty acid concentrate) was measured for POPs and cholesterol. Cholesterol was analyzed according to the European Pharmacopoeia Monograph 2.4.32, Total cholesterol in oils rich in omega-3 acids. The concentration of POPs was low and the concentration of total cholesterol (free plus esterified cholesterol) in the fatty acid concentrate was 0.06 mg/g. The levels of POPs in the K30EE starting material and in the resulting concentrate are shown in Table 11. As silver ions are known to interact with π-bond systems (see Table 4C) it could be anticipated that the level of persistent organic pollutants comprising aromatic ring systems would increase during the process. Benzo(a)pyrene showed a reduction of 74%. This indicates a weak complexation tendency with silver ions and that benzo(a)pyrene is not completely transferred to the water phase, but predominantly remains in the organic phase. Bearing in mind that the halogenated solvent showed a high ability to interact with the silver ion/poly unsaturated fatty acid complex (see Table 4C), surprisingly small amounts of the halogenated aromatics are transferred to the water phase and found in the concentrate. 96% or more of the halogenated aromatics added to the starting material are removed in the process.

TABLE 11

Levels of persistent organic pollutants in the starting material (K30EE added POPs) and concentrate.

| POP group | Name | Starting material | Concentrate |
|---|---|---|---|
| Dioxines | 2,3,7,8-TCDD | 18 pg/g | 0.36 pg/g |
| Non-ortho PCB | 3,3',4,4'-TeCB (PCB-77) | 249 pg/g | 7.0 pg/g |
| | 3,4,4',5-TeCB (PCB-81) | 12 pg/g | 0.30 pg/g |
| | 3,3',4,4',5-PeCB (PCB-126) | 6.3 pg/g | 0.18 pg/g |
| DDT | p,p'-DDT | 112 ng/g | 1.52 ng/g |
| PAH | Benzo(a)pyrene | 20 ng/g | 5.2 ng/g |

TABLE 11-continued

Levels of persistent organic pollutants in the starting material (K30EE added POPs) and concentrate.

| POP group | Name | Starting material | Concentrate |
|---|---|---|---|
| PBDE | DecaBDE | 4.7 ng/g | 0.19 ng/g |
| PCB | 2,2',4,4'-TetCB | 1.2 ng/g | 0.05 ng/g |
| | 2,2',5,5'-TetCB | 3.9 ng/g | 0.10 ng/g |
| | 2,3',4,4',TetCB | 2.2 ng/g | 0.04 ng/g |
| | 2,4,4',5-TetCB | 1.3 ng/g | 0.02 ng/g |
| | 2,2',4,4',5-PenCB | 1.0 ng/g | 0.02 ng/g |
| | 2,2',4,5,5'-PenCB | 3.7 ng/g | 0.08 ng/g |
| | 2,3,3',4,4'-PenCB | 1.0 ng/g | 0.02 ng/g |
| | 2,3,4,4',5-PenCB | 0.08 ng/g | <0.01 ng/g |
| | 2,3',4,4',5-PenCB | 2.1 ng/g | 0.04 ng/g |
| | 2,2',3,3',4,4'-HexCB | 0.7 ng/g | <0.01 ng/g |
| | 2,2',3,4,4',5'-HexCB | 29 ng/g | 0.65 ng/g |
| | 2,2',3,4,5,5'-HexCB | 1.3 ng/g | 0.02 ng/g |
| | 2,2',3,4',5',6-HexCB | 4.0 ng/g | 0.08 ng/g |
| | 2,2',4,4',5,5'-HexCB | 4.8 ng/g | 0.09 ng/g |
| | 2,3',4,4',5,5'-HexCB | 0.12 ng/g | <0.01 ng/g |
| | 2,2',3,3',4,4',5-HepCB | 1.7 ng/g | 0.03 ng/g |
| | 2,2',3,4,4',5,5'-HepCB | 6.0 ng/g | 0.11 ng/g |
| | 2,2',3,4,4',5',6-HepCB | 1.1 ng/g | 0.01 ng/g |
| | 2,2',3,4',5,5',6-HepCB | 2.9 ng/g | 0.06 ng/g |
| | 2,3,3',4,4',5,5'-HepCB | 0.04 ng/g | <0.01 ng/g |
| | 2,2',3,3',4,4',5,5'-OctCB | 1.3 ng/g | 0.02 ng/g |
| | 2,2',3,3',4,4',5,5',6-NonCB | 0.46 ng/g | <0.01 ng/g |
| | DecaCB | 0.04 ng/g | <0.01 ng/g |

Other than in the examples, or where otherwise indicated, all numbers expressing quantities of ingredients, reaction conditions, analytical measurements, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements.

What is claimed is:

1. A process for concentrating at least one omega-3 fatty acid from a fatty acid oil mixture, while reducing the concentration of at least one omega-6 fatty acid in the fatty acid oil mixture, the process comprising:

(a) combining the fatty acid oil mixture and an aqueous silver salt solution to form an aqueous phase and an organic phase, wherein in the aqueous phase, the aqueous silver salt solution forms a complex with the at least one omega-3 fatty acid;

(b) separating the aqueous phase from the organic phase;

(c) extracting the aqueous phase with a displacement liquid, or increasing the temperature of the aqueous phase to at least 30° C., or a combination of extracting with a displacement liquid and increasing the temperature, resulting in formation of at least one extract;

(d) combining the aqueous phase with water, or extracting the aqueous phase with supercritical $CO_2$, or a combination of combining the aqueous phase with water and extracting the aqueous phase with supercritical $CO_2$, to dissociate the complex, wherein an aqueous phase comprising the silver salt and at least one solution comprising a fatty acid concentrate forms; and (e) separating the at least one solution comprising the fatty acid concentrate from the aqueous phase comprising the silver salt, wherein the ratio of omega-3 to omega-6 fatty acids in the fatty acid concentrate is greater than about 40, greater than about 80, greater than about 100, greater than about 150, or greater than about 200.

2. The process according to claim 1, wherein the concentration of silver salt ranges from about 10% by weight in water to about 90% by weight in water.

3. The process according to claim 2, wherein the concentration of silver salt ranges from about 60% by weight to about 80% by weight in water.

4. The process according to claim 3, wherein the concentration of silver salt is about 60% by weight in water.

5. The process according to claim 1, wherein the silver salt is chosen from $AgNO_3$ and $AgBF_4$.

6. The process according to claim 1, wherein the at least one omega-3 fatty acid is chosen from (all-Z)–5,8,11,14,17-eicosapentaenoic acid (EPA), (all-Z)–4,7,10,13,16,19 docosahexaenoic acid (DHA), and combinations thereof.

7. The process according to claim 6, wherein the process concentrates EPA or DHA, or EPA and DHA.

8. The process according to claim 7, wherein the ratio of EPA/DHA in at least one of the fatty acid concentrate, the at least one extract, and the at least one solution ranges from about 0.1 to about 10 by weight.

9. The process according to claim 1, wherein the fatty acid concentrate comprises at least 90% omega-3 fatty acids by weight.

10. The process according to claim 6, wherein the fatty acid concentrate comprises at least 80% EPA and DHA by weight.

11. The process according to claim 1, wherein the total concentration of omega-6 fatty acids in the fatty acid concentrate is less than about 3% by weight.

12. The process according to claim 1, wherein the total concentration of omega-6 fatty acids in the fatty acid concentrate is less than about 2% by weight.

13. The process according to claim 1, wherein the total concentration of omega-6 fatty acids in the fatty acid concentrate is less than about 1% by weight.

14. The process according to claim 1, wherein the ratio of fatty acid oil mixture to the silver salt solution ranges from about 0.4 to about 1.6 by weight.

15. The process according to claim 1, wherein step (a) further comprises adding an alcohol to the aqueous phase.

16. The process according to claim 15, wherein the alcohol comprises ethanol.

17. The process according to claim 1, wherein the displacement liquid comprises an organic solvent.

18. The process according to claim 17, wherein the organic solvent is chosen from halogenated solvents, alkanes, alkenes, cycloalkanes, and cycloalkenes.

19. The process according to claim 17, wherein the organic solvent is chosen from dichloromethane, hexane, hexene, cyclohexane, cyclohexene, and dienes.

20. The process according to claim 1, wherein extracting the aqueous phase with the displacement liquid comprises at least two successive extractions.

21. The process according to claim 1, wherein the temperature of at least 30° C. ranges from about 30° C. to about 90° C.

22. The process according to claim 1, wherein combining the aqueous phase with water, or extracting the aqueous phase with supercritical $CO_2$, or a combination of combining the aqueous phase with water and extracting the aqueous phase with supercritical $CO_2$, to dissociate the complex is repeated at least once.

23. The process according to claim 1, wherein, following separation of the organic phase comprising the fatty acid concentrate, the silver salt is recovered from the aqueous phase comprising the silver salt for re-use.

24. The process according to claim 1, wherein the fatty acid oil mixture is derived from animal oils, vegetable oils, microbial oils, algae oils, or any combinations thereof.

25. The process according to claim 24, wherein the animal oil is a marine oil.

26. The process according to claim 25, wherein the marine oil is a fish oil.

27. The process according to any of claims 24-26, wherein the oil is in a form chosen from glyceride, ethyl ester, and free fatty acid forms.

28. The process according to claim 1, wherein the fatty acid concentrate comprises a reduced concentration of at least one environmental pollutant compared to the fatty acid oil mixture.

29. The process according to claim 1, wherein the fatty acid concentrate comprises a reduced concentration of cholesterol compared to the fatty acid oil mixture.

30. The process according to claim 1, wherein the at least one omega-3 fatty acid is in a form chosen from ethyl ester, free acid, and glyceride.

31. The process according to claim 1, wherein the fatty acid concentrate comprises a reduced concentration of at least one $C_{20}$-$C_{22}$ omega-3 fatty acid other than (all-Z)–5,8,11,14,17-eicosapentaenoic acid (EPA) and (all-Z)–4,7,10,13,16,19 docosahexaenoic acid (DHA) compared to the fatty acid oil mixture.

32. The process according to claim 31, wherein the total concentration of $C_{20}$-$C_{22}$ omega-3 fatty acids other than EPA and DHA in the fatty acid concentrate is less than 3% by weight.

33. The process according to claim 31, wherein the total concentration of $C_{20}$-$C_{22}$ omega-3 fatty acids other than EPA and DHA in the fatty acid concentrate is less than 2.5% by weight.

34. The process according to claim 31, wherein the total concentration of $C_{20}$-$C_{22}$ omega-3 fatty acids other than EPA and DHA in the fatty acid concentrate is less than 0.5% by weight.

35. The process according to claim 1, further comprising: (f) purifying the fatty acid concentrate through at least one purification process.

36. The process according to claim 35, wherein the at least one purification process is chosen from short-path distillation, molecular distillation, separation by iodolactonization, supercritical fluid extraction, enzymatic fractionation, and preparative chromatography.

37. The process according to claim 36, wherein the at least one purification process comprises short-path distillation and molecular distillation.

38. The process according to claim 1, wherein the process is repeated at least once wherein at least one of the fatty acid concentrate, the at least one extract, and the at least one solution comprises the fatty acid oil mixture in the subsequent process.

39. The process according to claim 38, wherein the process produces a fatty acid concentrate comprising at least 80% of at least one omega-3 fatty acid chosen from (all-Z)–5,8,11,14,17-eicosapentaenoic acid (EPA), (all-Z)–4,7,10,13,16,19-docosahexaenoic acid (DHA), and (all-Z)–7,10,13,16,19-docosapentaenoic acid (DPA).

40. The process according to claim 38, wherein the process produces a fatty acid concentrate comprising at least 90% of at least one omega-3 fatty acid chosen from EPA, DHA, and DPA.

41. The process according to claim 38, wherein the process produces a fatty acid concentrate comprising at least 95% of at least one omega-3 fatty acid chosen from EPA, DHA, and DPA.

42. The process according to claim 38, wherein the process produces a fatty acid concentrate comprising at least 98% of at least one omega-3 fatty acid chosen from EPA, DHA, and DPA.

43. The process according to claim 1, wherein at least one of the fatty acid concentrate, the at least one extract, and the at least one solution is treated by at least one fractionation process.

44. The process according to claim 43, wherein the at least one fractionation process is chosen from distillation, extraction, iodolactonization, and chromatography.

45. The process according to any one of claims 43-44, wherein the at least one fractionation process produces a fatty acid concentrate comprising at least 80% of at least one omega-3 fatty acid chosen from $C_{20}$-$C_{22}$ omega-3 fatty acids.

46. The process according to any one of claims 43-44, wherein the at least one fractionation process produces a fatty acid concentrate comprising at least 90% of at least one omega-3 fatty acid chosen from $C_{20}$-$C_{22}$ omega-3 fatty acids.

47. The process according to any one of claims 43-44, wherein the at least one fractionation process produces a fatty acid concentrate comprising at least 95% of at least one omega-3 fatty acid chosen from $C_{20}$-$C_{22}$ omega-3 fatty acids.

48. The process according to any one of claims 43-44, wherein the at least one fractionation process produces a fatty acid concentrate comprising at least 98% of at least one omega-3 fatty acid chosen from $C_{20}$-$C_{22}$ omega-3 fatty acids.

49. The process according to any one of claims 43-44, wherein the at least one omega-3 fatty acid is chosen from (all-Z)–4,7,10,13,16,19-docosahexaenoic acid (DHA) and (all-Z)–7,10,13,16,19-docosapentaenoic acid (DPA).

50. The process according to claim 1, wherein the fatty acid oil mixture comprises at least one persistent organic pollutant chosen from dioxines, PCBs, DDT, and PDBE.

51. The process according to claim 50, wherein the process reduces the at least one persistent organic pollutant in the fatty acid oil mixture by at least 95% in the fatty acid concentrate.

52. The process according to claim 1, wherein the fatty acid oil mixture comprises cholesterol.

53. The process according to claim 52, wherein the process reduces cholesterol in the fatty acid oil mixture to less than 0.1 mg/g in the fatty acid concentrate.

54. The process according to claim 1, wherein the supercritical $CO_2$ comprises at least one polar modifier.

55. The process according to claim 54, wherein the at least one polar modifier is chosen from water and an alcohol.

56. The process according to claim 1, wherein the fatty acid oil mixture and the aqueous silver salt solution are combined at a temperature ranging from about −25° C. to about 20° C., from about 20° C. to about 25° C., or from about 25° C. to about 90° C.

57. The process according to claim 1, wherein, following combining the fatty acid oil mixture and the aqueous silver salt solution, the aqueous phase is separated from the organic phase at a temperature ranging from about −25° C. to about 20° C., from about 20° C. to about 25° C., or from about 25° C. to about 90° C.

\* \* \* \* \*

UNITED STATES PATENT AND TRADEMARK OFFICE
CERTIFICATE OF CORRECTION

PATENT NO. : 9,145,533 B2
APPLICATION NO. : 13/825739
DATED : September 29, 2015
INVENTOR(S) : Harald Breivik et al.

It is certified that error appears in the above-identified patent and that said Letters Patent is hereby corrected as shown below:

IN THE CLAIMS

Col. 28, line 64, "omega-3fatty" should read --omega-3 fatty--.

Signed and Sealed this
Twenty-second Day of March, 2016

Michelle K. Lee
*Director of the United States Patent and Trademark Office*